> US006335353B1

United States Patent
Hider et al.

(10) Patent No.: US 6,335,353 B1
(45) Date of Patent: Jan. 1, 2002

(54) ORALLY ACTIVE IRON (III) CHELATORS

(75) Inventors: Robert Charles Hider, Clacton; Gary Stuart Tilbrook, Gerrards Cross; Zudong Liu, Catford, all of (GB)

(73) Assignee: BTG International Limited, London (GB)

( * ) Notice: Subject to any disclaimer, the term of this patent is extended or adjusted under 35 U.S.C. 154(b) by 0 days.

(21) Appl. No.: 09/437,211

(22) Filed: Nov. 10, 1999

Related U.S. Application Data

(63) Continuation of application No. PCT/GB98/01517.

(30) Foreign Application Priority Data

May 29, 1997 (GB) .................................... 9711093

(51) Int. Cl.$^7$ .................................. A01N 43/40
(52) U.S. Cl. .......................... 514/348; 546/296; 548/182
(58) Field of Search .............................. 546/296; 514/348

(56) References Cited

U.S. PATENT DOCUMENTS 5,112,968 A  *  5/1992  Treuner ........................ 540/355

FOREIGN PATENT DOCUMENTS

| BE | 651 427 A | 2/1965 |
| EP | 0 768 302 A | 4/1997 |
| FR | 1 516 463 A | 6/1968 |
| GB | 2 242 191 A | 9/1991 |

OTHER PUBLICATIONS

Singh et al. "Urinary metabolic profiles in human and rat of 1,2–dimethyl– and . . . ," Drug Metabolism and Disposition, vol. 20, No. 2, pp. 256–261 (1992).

(List continued on next page.)

Primary Examiner—Alan L. Rotman
(74) Attorney, Agent, or Firm—Nixon & Vanderhye

(57) ABSTRACT

A novel 3-hydroxypyridin-4-one compound of formula I is provided wherein
R is hydrogen or a group that is removed by metabolism in vivo to provide the free hydroxy compound,
$R^1$ is an aliphatic hydrocarbon group or an aliphatic hydrocarbon group substituted by a hydroxy group or a carboxylic acid ester, sulpho acid ester or a $C_{1-6}$ alkoxy, $C_6$-aryloxy or $C_{7-10}$aralkoxy ether thereof,
$R^3$ is selected from hydrogen and $C_{1-6}$alkyl;
and $R^4$ is selected from hydrogen, $C_{1-6}$alkyl and a group as described for $R^2$;
characterised in that
$R^2$ is selected from groups

| —CONH—$R^5$ | (i) |
| —CH$_2$NHCO—$R^5$ | (ii) |
| —SO$_2$NH—$R^5$ | (iii) |
| —CH$_2$NHSO$_2$—$R^5$ | (iv) |
| —CR$^6$R$^6$OR$^7$ | (v) |
| —CONHCOR$^5$ | (viii) | wherein
$R^5$ is selected from hydrogen and optionally hydroxy, alkoxy, or aralkoxy substituted $C_{1-13}$ alkyl, aryl and $C_{7-13}$ aralkyl,
$R^6$ is independently selected from hydrogen, $C_{1-13}$ alkyl, aryl and $C_{7-13}$ aralkyl,
and $R^7$ is selected from hydrogen, $C_{1-13}$ alkyl, aryl and $C_{7-13}$ aralkyl or a pharmaceutically acceptable salt of any such compound
with the proviso that when $R^7$ is hydrogen, $R^6$ is not selected from aryl and with the proviso that the compound is not 1-ethyl-2-(1'-hydroxyethyl)-3-hydroxypyridin-4-one.

11 Claims, 3 Drawing Sheets

OTHER PUBLICATIONS

Rodrigues et al., "Chelating agent inhibition of Trypanosoma . . . ," Journal of Inorganic Biochemistry, vol. 60, No. 4, pp. 277–288 (1995).

Chemical Abstracts No. 70546p, vol. 96, No. 10 (1982).

Kimura et al, "Central depressant effects of maltol analogs . . . ," Chemical and Pharmaceutical Bulletin, vol. 28, No. 9, pp. 2570–2579 (1980).

Chemical Abstracts No. 87703f, vol. 74, No. 17, p. 414 (1971).

* cited by examiner

ORALLY ACTIVE IRON (III) CHELATORS

This Application is a Continuation of PCT/GB98/01517 filed May 26, 1998.

The present invention relates to novel compounds having activity as orally active iron chelators, to pharmaceutical compositions containing these and to their use in treating disorders associated with iron distribution, particular disorders involving excess of iron and presence of iron dependent parasites.

Members of the hydroxypyridone class are well known for their ability to chelate iron in physiological environment and these have reported as useful in treating iron related disorders such as thalassaemia and, when complexed with iron, anaemia. For example, see U.S. Pat. Nos. 4,840,958, 5,480,894 and Hider et al (1996) Acta Haematologica 95:6–12. By virtue of their low molecular weight and high affinity for iron (III) these compounds now provide the possibility of removing iron from iron overloaded patients with the hope of providing oral activity. Related compounds for such use are disclosed in U.S. Pat. No. 4,585,780 wherein the characteristics required for oral activity are discussed further.

Two particular compounds referred to by Hider et al, CP20 and CP94 (see Tables 1 and 2 herein), have proved to be effective in man, but both have disadvantages in that they are rapidly inactivated by phase II metabolism and are able to cross the placenta and blood brain barrier. The extensive biotransformation of these compounds is reflected by their limited ability to mobilise excess body iron in thalassaemic patients.

The requirements for orally active chelators are set out in Table 4 of Hider et al as (i) good absorption from the gastrointestinal tract, (ii) efficient liver extraction, (iii) poor entry into peripheral cells such as thymus, muscle, heart and bone marrow and (iv) poor ability to penetrate the blood-brain barrier and maternal/placental barriers. This reference refers to desired partition coefficients ($K_{part}$), herein referred to as distribution coefficient values ($D_{pH7.4}$) for these properties as (i) >0.2, (ii) >1.0, (iii) <0.001 and (iv) <0.001, respectively rendering one compound seemingly unsuited to satisfying all four criteria. Hider et suggest the pro-drug strategy to be one possible route forward but no specific compounds have so far been found to meet all criteria.

Pivalic acid esters of hydroxyalkyl substituted 3-hydroxypyridin-4-ones have been studied as pro drugs and found to lead to efficient excretion of iron, in bile and urine, but as reported by Hider et al these are now thought to potentially interfere with the carnitine cycle and thus may not be suitable for use in regular and/or large doses in man.

It is known that the 2-(1'-hydroxyethyl) metabolite of 1,2-diethyl-3-hydroxypyridin-4-one (CP94) produced in rat is an active iron chelator (see Singh et al (1992) Drug Metabolism and Disposition Vol 20. No 2, page 256–261). EP 0494754 A proposes 1-hydroxyethyl as one of many possible substituents at any of the pyridin-4-one positions 1, 2, 5 or 6 for use as iron chelator in treatment of malaria; none of these compounds are however exemplified as made or tested for activity. EP 0768302 A (Novartis) describes a series of related 3-hydroxypyridin-4-ones in which the 2-position is substituted by a methyl group which carries an optionally substituted phenyl or heteroyl ring and a free or esterified hydroxy group. The phenyl or heteroyl group is taught as an essential element of these compounds.

The present inventors now have provided a group of 3-hydroxypyridin-4-one iron chelators having improved properties as compared to the prior art as assessed against the criteria set out above. The preferred compounds of the invention are all characterised by meeting a further criterion (v) in so far as they have a pM for Iron III, i.e. affinity for iron as Fe III, of at least 20, preferably in excess of 23. Preferred compounds have efficiency of iron mobilisation of in excess of 52% when given orally to rats. The definition of pM used herein is the concentration of ferric ion in solution when the total amount of iron equals $10^{-6}$ M and the concentration of ligand is $10^{-5}$ M and pH is 7.4.

The present compounds offer the prospect of effective pharmaceutical formulations having reduced levels of active agent, with particular properties of selective targeting of the chelating activity to tissues where the iron level requires alteration, particularly the liver. A particular property of preferred compounds of the invention is that they are not significantly metabolised through conjugation and, in preferred forms, are provided as prodrugs.

Thus in a first aspect of the present invention there is provided a novel 3-hydroxypyridin-4-one compound of formula I

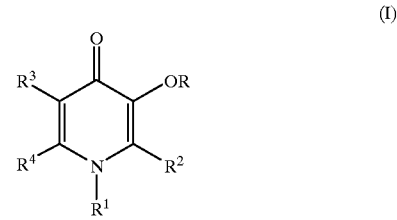

(I)

wherein
R is hydrogen or a group that is removed by metabolism in vivo to provide the free hydroxy compound,
$R^1$ is an aliphatic hydrocarbon group or an aliphatic hydrocarbon group substituted by a hydroxy group or a carboxylic acid ester, sulpho acid ester or a $C_{1-6}$ alkoxy or $C_{7-10}$ aryloxy or aralkyloxy ether thereof,
$R^3$ is selected from hydrogen and $C_{1-6}$ alkyl;
and $R^4$ is selected from hydrogen, $C_{1-6}$ alkyl and a group as described for $R^2$;
characterised in that
$R^2$ is selected from groups

| | |
|---|---|
| —CONH—$R^5$ | (i) |
| —CH$_2$NHCO—$R^5$ | (ii) |
| —SO$_2$NH—$R^5$ | (iii) |
| —CH$_2$NHSO$_2$—$R^5$ | (iv) |
| —CR$^6$R$^6$OR$^7$ | (v) |
| —CONHCOR$^5$ | (viii) | wherein
$R^5$ is selected from hydrogen and optionally hydroxy, alkoxy, aryloxy or aralkoxy substituted $C_{1-13}$ alkyl, aryl and $C_{7-13}$ aralkyl,
$R^6$ is independently selected at each occurrence from hydrogen, $C_{1-13}$ alkyl, aryl and $C_{7-13}$ aralkyl,
and $R^7$ is selected from hydrogen, $C_{1-13}$ alkyl, aryl and $C_{7-13}$ aralkyl or a pharmaceutically acceptable salt of any such compound
with the proviso that when $R^7$ is hydrogen, $R^6$ is not selected from aryl,
and with the proviso that the compound is not 1-ethyl-2-(1'-hydroxyethyl)-3-hydroxypyrid-4-one.

Preferably at least one of R, $R^1$ or $R^7$ is such as to form a 3-ester or ether prodrug. Those skilled in the art will recognise the term 3-ester or ether prodrug to mean compounds wherein the 3-hydroxy group has been esterified with a carboxylic or sulpho acid, or formed into an ether with a $C_{1-6}$ alkyl or $C_{1-10}$ aralkyl group which is removed in vivo to provide the free hydroxy compound. Typically such carboxylic acid esters or ethers are of $C_{1-7}$ type, ie. the 3-substituent is —O—$R^8$ or —OC(O)—$R^8$ where $R^8$ is $C_{1-6}$ alkyl or $C_{1-10}$ aralkyl.

More preferably $R^5$ and $R^7$ are independently selected from $C_{1-6}$ alkyl, aryl or aralkyl, e.g. benzyl, which may be substitued with $C_{1-6}$ alkoxy. More preferably $R^6$ is independently selected from hydrogen or $C_{1-6}$ alkyl.

The positions 5 and 6 are preferably unsubstituted, ie. $R^3$ and $R^4$ are preferably hydrogen, but may be substituted with conventional pyridin-4-one substituents as disclosed by the prior art as suitable in iron chelators.

Where $R^1$ is an aliphatic carbon group substituted by hydroxy and that hydroxy is esterified the ester acyl group is preferably of formula —CO—$R^9$ where $R^9$ is $C_{1-6}$ alkyl or $C_{1-10}$ aryl, more preferably being —CO-Phenyl or —CO-hetero, eg. heterocylic rings with one of two nitrogen members and three to five carbons.

$R^1$ and $R^5$ are conveniently independently selected $C_{1-6}$alkyl, preferably methyl or ethyl, but preferably may be a hydroxy, alkoxy or esterified hydroxy terminated $C_{1-6}$ alkyl group. Where $R^1$ is a hydroxy terminated alkyl it is advantageous that the alkyl group is of 3 to 6 carbons long, more preferably being 3 carbons long, e.g. where $R^1$ is —(CH$_2$)$_3$—OH, as such compounds are known to be metabolised in vivo to the corresponding —(CH$_2$)$_2$—CO$_2$H derivative with consequent advantages of low $D_{pH7.4}$ after metabolism, e.g. in the liver.

Most preferred compounds are of the type where $R^2$ is of groups (i), or (v).

More preferably $R^2$ is a group —CR$^6$R$^6$OR$^7$ wherein $R^6$ is independently selected at each occurrence from hydrogen, $C_{1-13}$ alkyl or $C_6$ aryl and $R^7$ is $C_{1-6}$ alkyl, more preferably methyl or ethyl. An alternate preferred group for $R^2$ is —CONH—$R^5$.

Still more preferred compounds of the invention have a $D_{pH7.4}$ as determined in an octanol/MOPS pH 7.4 system of in excess of 1, more preferably being metabolised in vivo to a metabolite having a $D_{pH7.4}$ of less than 1, more preferably less than 0.1 and still more preferably less than 0.001, as set out in the criteria above.

A second aspect of the present invention provides processes for preparation of new compounds of the invention, a third provides novel intermediates for use in these processes, a fourth provides the use of the compounds in therapy, a fifth provides their use in manufacture of medicaments and a sixth provides pharmaceutical compositions comprising them.

The process of the invention is broadly that as set out in any one or more of Schemes 1, 2, 3 and 4. The preferred process comprises all relevant steps of these schemes for a given compound of the invention. Those skilled in the art will readily produce free compounds from the salts shown by conventional techniques.

Novel intermediates of the invention are of formula (IIb), (IIc) and (III) of Scheme 1 (IVa), (IVb) and (IVc) of Scheme 2, (VI), (VII) and (VIII) of Scheme 3 and (X), (XI), (XII) of Scheme 4.

Thus a first process of the invention comprises the reaction of a 2-(1'-hydroxyalkyl)-3-hydroxy-pyran-4(1H)-one of formula (IIa)

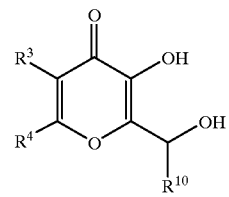

(IIa)

where $R^{10}$ is a group as defined in $R^6$ with benzaldehyde dimethyl acetal to provide the corresponding 8-oxo-4,8-dihydro-2-phenyl-4H[3,2-d]-m-dioxin of formula (IIb),

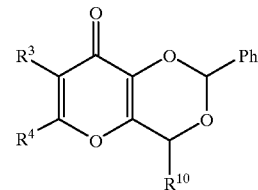

(IIb)

reacting that compound with a compound $R^1NH_2$ to give the corresponding pyridino dioxin of formula (IIc)

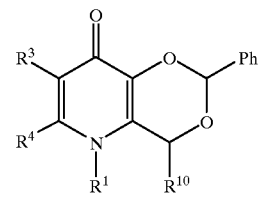

(IIc)

and reducing that with hydrogen to give the corresponding 2-hydroxyalkyl-pyridin-4(1H)-one.

A second process of the invention comprises the protection of the 3-hydroxyl group of a 2-(1'-hydroxyalkyl)-3-hydroxy-pyran-4(1H)-one of formula (IV),

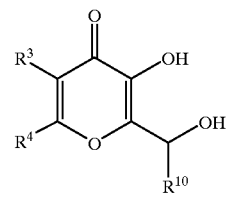

(IV)

eg. using a benzyl halide, preferably benzyl bromide to give a compound (IVa)

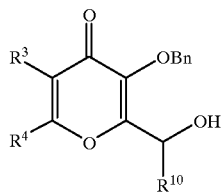
(IVa)

alkylating the 2-(1'-hydroxy) group, eg. with an alkyl halide such as alkyl iodide to, reacting the product thereof (IVb)

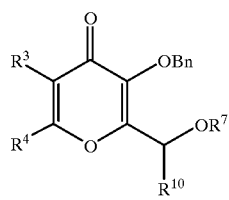
(IVb)

with a compound $R^1NH_2$ to provide the corresponding 2-hydroxyalkyl-pyridin-4(1H)-one (IVc)

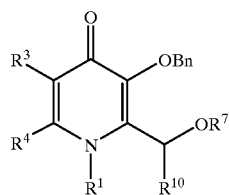
(IVc)

and reducing that to provide the correpsonding unprotected compound.

A third process of the present invention reacts a 2-carboxyl-3-benzoyloxy-pyran-4(1H)-one of formula (IXd), that optionally being provied by oxidising the corresponding formyl compound (IXc) eg. with sulfamic acid and sodium chlorite,

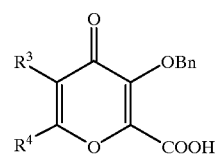
(IXd)

with mercaptothiazoline, eg. in the presence of dicyclocarbodiimide and dimethylaminopyridine to provide the corresponding 2-carbonyl-thiazolidine-2-thione of formula (X),

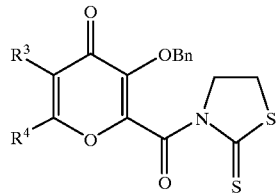
(X)

reacts that with a compound $R^5NH_2$ to give the corresponding 2-amido compound of of formula (XI),

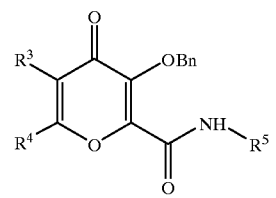
(XI)

reacting that with a compound $R^1NH_2$ to give the corresponding 2-amido-pyridin-4(1H)-one compound of formula (XII)

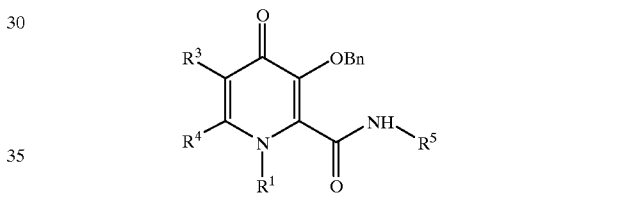
(XII)

and optionally reducing that to provide the corresponding 2-hydroxyalkyl-pyridin-4(1H)-one.

Novel intermediates are the 8-oxo-4,8-dihydro-2-phenyl-4H[3,2-d]-m-dioxins, 2-(1-alkoxyoxyalkyl)-3-hydroxy-pyran-4(1H)-ones and corresponding 2-carbonyl-thiazolidine-2-thiones corresponding to the compounds of Formula I.

Also provided within formula (I) are novel compounds which are metabolites of the preferred prodrug compounds of the first aspect of the invention but which have $D_{pH7.4}$ less than 1; these also being active iron III chelating agents once the compounds of the first aspect have been metabolised eg. in the liver, to remove any ether or ester protecting group where that was required to provide a $D_{pH7.4}$ of 1 or above. For example in compound CP362 below, the methyl group (R in formula I above), is removed in vivo resulting in a drop in $D_{pH7.4}$ to give the compound of formula I wherein R is hydrogen, $R^2$ is $CH(OH)CH_3$, $R^1$ is ethyl and $R^3$ and $R^4$ are hydrogen. This compound 1-ethyl-2-(1'-hydroxyethyl)-3-hydroxypyrid4-one is known.

Those skilled in the art will readily appreciate that some of these compounds will be known already, but in so far as compounds are novel they are also rendered inventive by their relationship as active metabolites of the novel compounds of the first aspect. Particularly provided is the provision of such metabolites 'for use in therapy' eg. 'for use in therapy of iron related disorders'. These compounds, while not of ideal $D_{pH7.4}$ for oral activity, will still be of potential use by parenteral or other route of administration.

Salts of the compounds of the invention may readily be formed by reaction of the compound with the appropriate base or acid under suitable conditions. Zwitterionic forms, where appropriate, may conveniently be obtained by freeze drying an aqueous solution at a selected pH. Freeze drying of an aqueous solution whose pH has been adjusted to 7.0 or to greater than 9.0 with the desired base provides a convenient route to a salt of that base. Salts with acids may conveniently be obtained by recrystallization of the compound of formula (I) from an aqueous/organic solution, for example the hydrochloride being obtained on recrystallization from a dilute hydrochloric acid/ethanol solution.

Pro-drugs may be formed by reaction of any free hydroxy group compound of formula (I) or a derivative thereof with the appropriate reagent, in particular with an organic acid or derivative thereof, for example as described in U.S. Pat. No. 4,908,371 and/or with an alcohol or phenol, for example using standard esterification procedures.

The compounds of formula (I) may be formulated with a physiologically acceptable diluent or carrier for use as pharmaceuticals for veterinary, for example in a mammalian context, and particularly for human use, by a variety of methods. For instance, they may be applied as a composition incorporating a liquid diluent or carrier, for example an aqueous or oily solution, suspension or emulsion, which may often be employed in injectable form for parenteral administration and therefore may conveniently be sterile and pyrogen free. Oral administration is preferred for the preferred compounds of the invention. Although compositions for this purpose may incorporate a liquid diluent or carrier, it is more usual to use a solid, for example a conventional solid carrier material such as starch, lactose, dextrin or magnesium stearate. Such solid compositions may conveniently be of a formed type, for example as tablets, capsules (including spansules), etc.

Other forms of administration than by injection or through the oral route may also be considered in both human and veterinary contexts, for example the use of suppositories or pessaries. Another form of pharamceutical composition is one for buccal or nasal administration, for example lozenges, nose drops or an aerosol spray. Thus, the invention further includes a pharmaceutical composition comprising a 3-hydroxypyridin-4-one drug or prodrug of formula (I) as defined hereinbefore together with a physiologically acceptable diluent or carrier.

Compositions may be formulated in unit dosage form, i.e. in the form of discrete portions each comprising a unit dose, or a multiple or sub-multiple of a unit dose. The dosage of active compound given will depend on various factors, including the particular compound employed in the composition and the mode of administration and type of disease be treated, eg. whether for iron overload as in thalessemia or for use in treating iron dependent parasites eg. malaria.

Typical dosages for use in human therapy will usually lie in the region of about 0.1 to 50 g daily, preferably 0.5 g to 20 g daily, particularly from about 1 or 2 g to 10 or 15 g daily, for example about 5 g, veterinary doses being on a similar g/kg body weight ratio. However, it will be appreciated that it may be appropriate under certain circumstances to give daily dosages either below or above these levels. Where desired, more than one compound according to the present invention may be administered in the pharmaceutical composition, when the total dosage will usually correspond to those discussed above, or, indeed, other active compounds may be included in the composition.

The present invention will now be described by way of illustration only by reference to the following non-limiting Examples, Tables, Schemes and Figures. Further examples of the invention will occur to those skilled in the art in the light of these.

TABLES

Table 1: shows compound codes, structures, $D_{pH7.4}$ (also known as Kpart), pKa, Log$\beta$3, pM and in vivo iron mobilisation data for compounds of the invention where $R^2$ is of type (v), both active agents for oral administration and their metabolites, the latter being suitable for parenteral or other non-oral route administration.

Table 2: summarises Table 1 with significant pKa2 and comparative data added.

Table 3: shows compound codes structures, $D_{pH7.4}$ (also known as Kpart), pKa, Log$\beta$3, pM and in vivo iron mobilisation data for compounds of the invention where $R^2$ is of type (i).

SCHEMES

Scheme 1 shows the reaction scheme for synthesis of novel intermediates from compounds of formula (IIa) to compounds of formula (III)

Scheme 2 shows the reaction scheme for synthesis of novel intermediates from compounds (IV) to orally active compounds (V) and Scheme 3 shows the reaction scheme for formation of $R^1$ ester type oral active compounds.

Scheme 4 shows the reaction scheme for synthesis of novel intermediates from compounds (IX) to amide products (XII) and (XIII).

SYNTHESIS

Known Intermediates 2,5-Dihydro-2,5-dimethoxy-2-furanmethanol

Figure 1:
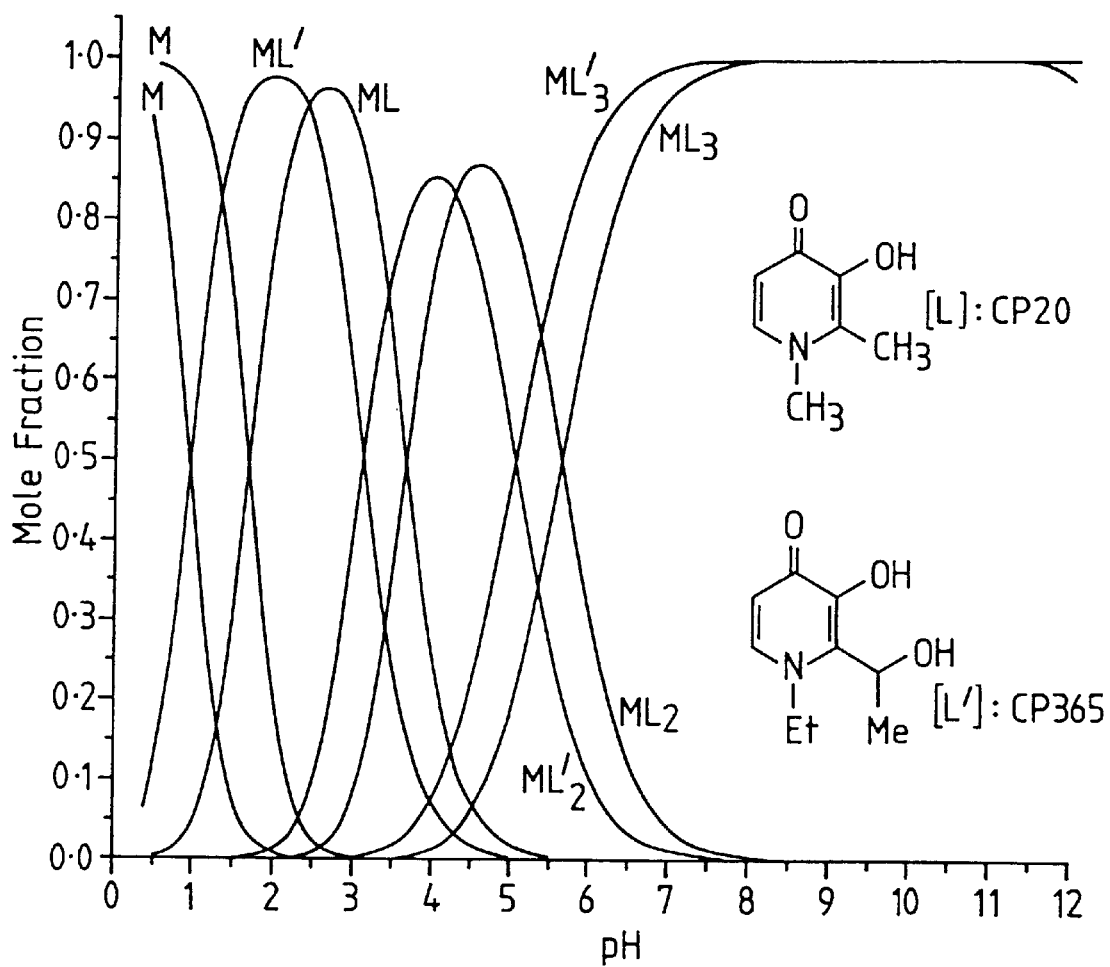
FIG. 1 shows a speciation plot of ratio of ligand to Iron (III) v pH.
Figure 2:
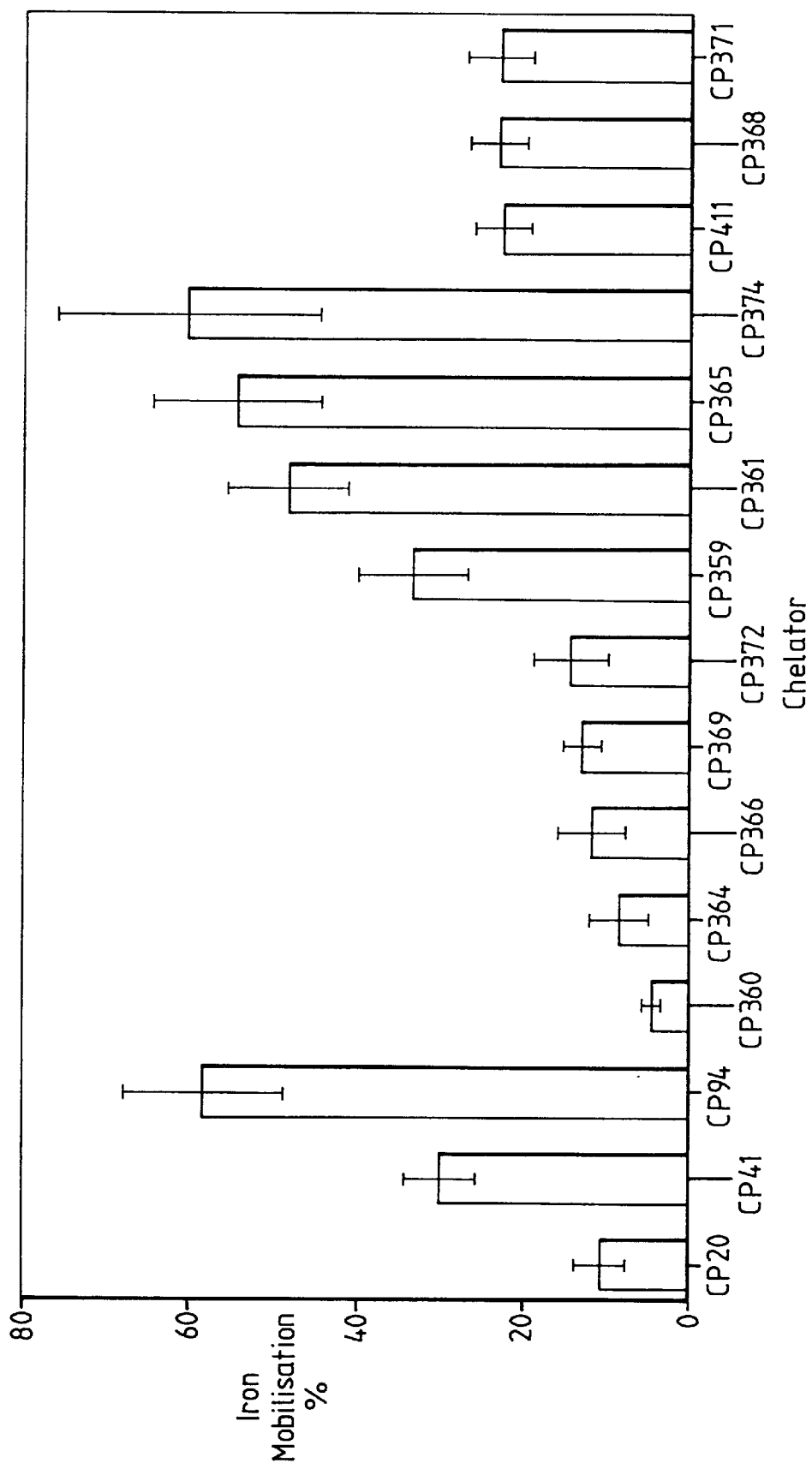
FIG. 2 shows in vivo iron mobilisation using the metabolite free hydroxy compounds of the invention.
Figure 3:
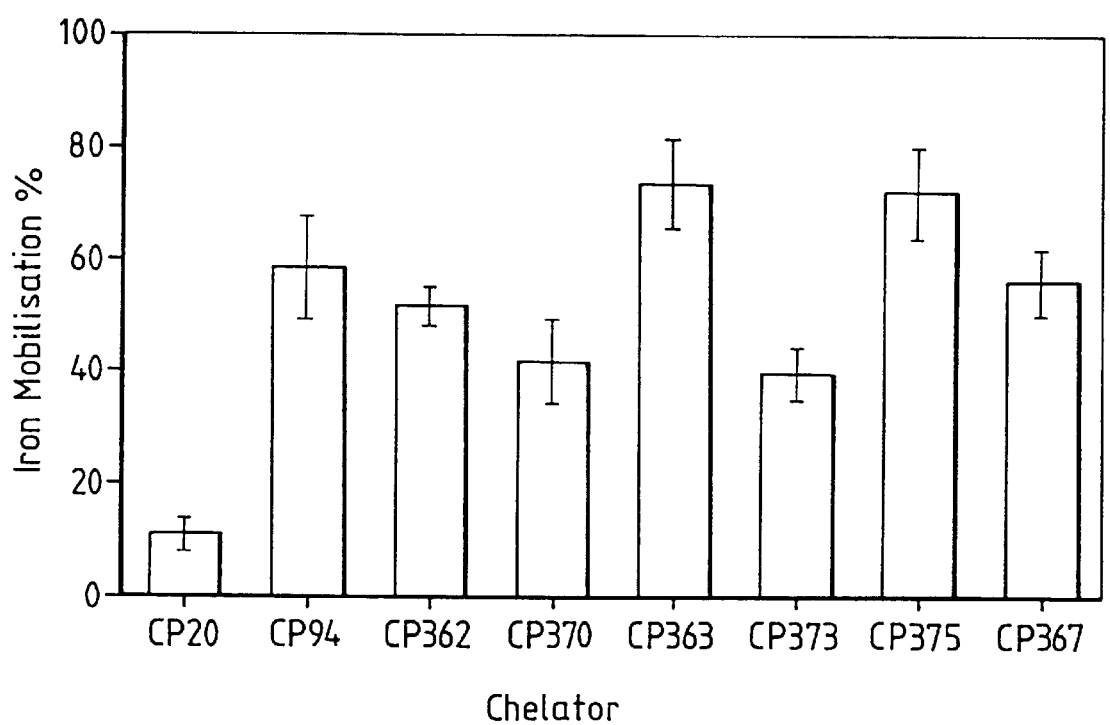
FIG. 3 shows in vivo iron mobilisation using the orally active ether compounds of the invention.

Produced by the method of Achamatowicz et al (1971) Tetrahedron; 27:1973–1996. Distillation at 78° C./0.5 mmHg (Lit. $^{(a)}$71° C./1.0 mmHg; gave the title compound (177 g, 73.8%) as colorless liquid.

Evaporation of the solvent and distillation at 74° C./0.4 mmHg gave title product as colorless liquid. (115.5 g, 72.2%).

6-Methoxy-2H-pyran-3(6H)-one

Produced by the method of of Achamatowicz et al (1971). Distillation at 47~48° C./0.5 mmHg (lit. 76~81° C./13 mmHg) afforded a clear, sharp-smelling oil.

Novel Intermediate

4-Bromo-6-methoxy-2H-pyran-3(6H)-one

To a solution of 6-methoxy-2H-pyran-3(6H)-one 12.8 (0.1 mole) in 40 ml $CH_2Cl_2$ at 0° C. was added 16.0 g (0.1 mole) of bromine in 10 ml of $CH_2Cl_2$. Then 14 ml of triethylamine was added dropwise at 0° C. and the reaction was allowed to warm to room temperature and stir for two hours. The reaction was then diluted with 200 ml of toluene. After filtration, the organic solution was then washed with 5% $NaHCO_3$ and brine, dried with $Na_2SO_4$, filtered and concentrated to yield the crude product as light brown solid.

Recrystallisation from ethyl acetate afforded the title compound (17 g, 82%) as a white crystalline solid. m.p. 74–75° C.

$^1$H-NMR (CDCl$_3$) δ: 3.5 (s, 3H, OCH$_3$), 4.4 (q, 2H, 2,2'-H, AB center, J$_{22'}$=14.5 Hz, δ$_{22'}$=18.5 Hz), 5.05 (d, 1H, 6-H), 7.25 (d, 1H, 5-H)

Anal. Calcd. for C$_6$H$_7$O$_3$Br: C, 34.81; H, 3.41%. Found: C, 35.03; H, 3.45%.

Recrystallisation from ethyl acetate afforded the title compound (17 g, 82%) as a white crystalline solid. m.p. 74–75° C.

Anal. Calcd. for C$_6$H$_7$O$_3$Br: C, 34.81; H, 3.41%. Found: C, 35.03; H, 3.45%.

Known Intermediates

3-Hydroxy-pyran-4(1H)-one (pyromeconic acid)

The solid was treated with activated carbon and recrystallised from toluene to yield the title compound (2.5 g, 80%) as a light yellow plates. m.p. 114–115° C. [lit. 113–115.5 ° C. (Tate and Miller., 1964) U.S. Pat. No. 3,130,204].

6-Chloromethyl-3-hydroxy-pyran-4(1H)-one (chlorokojic acid)

The product was collected by filtration and washed with petroleum ether and then recrystallised from water to give the pure title compound (42.5 g, 75.9%) as colourless needles. m.p. 166–168° C. [lit. 166–167° C.: Tilbrook G Thesis Kings College London.1995].

3-Hydroxy-6-methyl-pyran-4(1H)-one (allomaltol)

Recrystallisation from isopropanol afforded 14.8 g (62.8%) of analytically pure allomaltol as colourless plates. m.p. 152–153° C. [lit. 152–153° C. Tibrooke G Thesis as above].

2-Hydroxymethyl-3-hydroxy-pyran-4(1H)-one (α-hydroxymaltol)

Sodium hydroxide (4 g, 100 mmol, 1.25 eq.) dissolved in 10 ml distalled water was added to a solution of 3-hydroxy-pyran-4(1H)-one (8.96 g, 80 mmol, 1 eq.) in 50 ml methanol and allowed to stir at room temperature for 5 minutes. 16 ml (200 mmol, 2.5 eq.) of 35% formaldehyde solution was added dropwise over 15 minutes and the solution was stirred overnight. After adjustment to pH 1 with 37% w/v hydrochloric acid, the reaction mixture was concentrated in vacuo to dryness and the resulting solid was extracted with 2×100 ml of isopropanol at 90° C. The isopropanol extracts were concentrated to yield the crude products. Recrystallisation from isopropanol afforded 9.7 g (85.4%) of the pure title product as a white crystalline solid. m.p. 154–156° C. [lit. 148–150° C. (Tate and Miller., 1964)].

$^1$H-NMR (DMSO-d$_6$) δ: 4.4 (s, 2H, 2-CH$_2$OH), 4.6–5.7 (br., 1H, 2-CH$_2$OH), 6.34 (d, 1H, 5-H), 8.1 (d, 1H, 6-H), 9.0 (br., s, 1H, 3-OH)

2-(1-Hydroxyethyl)-3-hydroxy-pyran-4(1H)-one

3-Hydroxy-pyran-4(1H)-one (5.6 g, 50 mmol, 1 eq.) was added to 50 ml water and the pH of the solution was adjusted to 10.5 using 50% aqueous sodium hydroxide. Acetaldehyde (2.64 g, 60 mmol, 1.25 eq.) dissolved in 20 ml water was slowly added dropwise over 1 hour and the solution allowed to stir overnight. The reaction mixture was acidified to pH 1 with 37% w/v hydrochloric acid and concentrated in vacuo to dryness. The residue was extracted with 2×70 ml of isopropanol at 90° C. The isopropanol extracts were combined and concentrated to yield after recrystallisation from toluene, the pure product (3.7 g, 47.4%) as a pale yellow crystalline solid. m.p. 131–132° C. [lit. 130—131° C. (Ichimoto, 1970)].

$^1$H-NMR (DMSO-d6) δ: 1.3 (d, 3H, 2-CHCH$_3$), 5.03 (q, 1H, 2-CHCH$_3$), 6.38 (d, 1H, 5-H), 8.2 (d, 1H, 6-H)

2-Hydroxymethyl-3-hydroxy-6-methyl-pyran-4(1H)-one

Allomaltol (12.6 g, 100 mmol, 1 eq.) was added to an aqueous solution containing 4.4 g (110 mmol, 1.1 eq.) of sodium hydroxide in 100 ml distilled water and stirred at room temperature for 5 minutes. 9 ml (110 mmol, 1.1 eq.) of 35% w/v formaldehyde solution was added dropwise over 10 minutes and the solution allowed to stir overnight. Acidification to pH 1 using concentrated hydrochloric acid and cooling to 3–5° C. for 12 hours gave a crystalline deposit. The title product was isolated by filtration as colourless needles (12.8 g, 82%). m.p. 159–161° C. [lit. (1): 157–158° C.; lit. (2): 161–163° C.]Tilbrook (1993) Recrystallisation solvent ethanol.

$^1$H-NMR (DMSO-d$_6$) δ: 2.30 (s, 3H, 6-CH$_3$), 4.5 (s, 2H, 2-CH$_2$OH), 4.6–5.7 (br., 1H, 2-CH$_2$OH), 6.25 (s, 1H, 5-H), 8.7–9.2 (br., 1H, 3-OH)

2-(1-Hydroxyethyl)-3-hydroxy-6-methyl-pyran-4(1H)-one

Allomaltol (12.6 g, 100 mmol, 1 eq.) was added to 100 ml water and the pH of the solution was adjusted to 10.5 using 50% aqueous sodium hydroxides. Acetaldehyde (5.5 g, 125 mmol, 1.25 eq.) dissolved in 25 ml water was slowly added dropwise over 1 hour and the solution allowed to stir overnight. After adjustment to pH 1 with 37% hydrochloric acid, the reaction mixture was extracted with 3×150 ml of dichloromethane. The combined organic extracts were dried over anhydrous sodium sulphate, filtered and concentrated to yield the crude product. Recrystallisation from toluene afforded the pure product (14.1 g, 83%) as white needles. m.p. 127–130° C. [lit. 126–128° C.]. Ellis (1993)

$^1$H-NMR (DMSO-d$_6$) δ: 1.25 (d, 3H, 2-CHCH$_3$), 2.2 (s, 3H, 6-CH$_3$), 4.9 (q, 1H, 2-CHCH$_3$), 5.2 (br., s, 1H, 2-CHOH), 6.1 (s, 1H, 5-H), 8.6 (br., s, 1H, 3-OH)

2-(1-Hydroxypropyl)-3-hydroxy-6-methyl-pyran-4(1H)-one

Allomaltol (12.6 g, 100 mmol, 1 eq.) was added to 100 ml water and the pH of the solution was adjusted to 10.5 using 50% aqueous sodium hydroxides. Propionaldehyde (8.7 g, 150 mmol, 1.5 eq.) dissolved in 50 ml methanol was slowly added dropwise over 1 hour and the solution allowed to stir at room temperature for 48 hours. After adjustment to pH 1 with 37% hydrochloric acid, the reaction mixture was evaporated to dryness and the residue taken up into 300 ml of dichloromethane. The organic layer was washed with water (150 ml), dried over anhydrous sodium sulphate, filtered and concentrated to yield the crude product. Recrystallisation from toluene afforded the pure product (14.5 g, 78.9%) as a white crystalline solid. m.p. 134–136° C. [lit. 132–135° C. Ellis (1993)].

$^1$H-NMR (CDCl$_3$) δ: 1.12 (t, 3H, 2-CHCH$_2$CH$_3$), 1.7–2.3 (m, 2H, 2-CHCH$_2$CH$_3$), 2.45 (s, 3H, 6-CH$_3$), 4.95 (q, 1H, 2-CHCH$_2$CH$_3$), 5.0–6.0 (br., 1H, 2-CHOH), 6.3 (s, 1H, 5-H)

Novel Intermediates

EXAMPLE 1

8-Oxo-4,8-dihydro-2-phenyl-4H-pyrano[3,2-d]-m-dioxin

A solution of 2-hydroxymethyl-3-hydroxy-pyran-4(1H)-one (2.84 g, 20 mmol, 1 eq.), benzaldehyde dimethyl acetal (6.08 g, 40 mmol, 2 eq.) and toluene-p-sulphonic acid monohydrate (0.04 g, cat.) in 50 ml DMF was rotated under aspirator pressure at 80°C. for 3 hours. The solvent was removed under high vacuum, the residue taken up into 100 ml dichloromethane. The organic solution was washed successively with aqueous $Na_2CO_3$ and brine. After drying over magnesium sulphate, the solvent was removed to give the crude product. Recrystallisation from $CH_2Cl_2$/Pet. ether 40/60 afforded the pure title compound (3.77 g, 82%) as a white crystalline solid. m.p. 141–143° C.

$^1$H-NMR (CDCl$_3$) δ: 4.72 (d, 2H, CH$_2$O), 5.88 (s, 1H, CHPh), 6.35 (d, 1H, 7-H(pyranone)), 7.2–7.9 (m, 6H, Ar & 6-H(pyranone))

Anal. Calcd. for $C_{13}H_{10}O_4$: C, 67.82; H, 4.38%. Found: C, 68.13; H, 4.26%.

EXAMPLE 2

8-Oxo-4,8-dihydro-4-methyl-2-phenyl-4H-pyranol[3,2-d]-m-dioxin

In an analogous procedure in the preparation of 8-oxo-4,8-dihydro-2-phenyl-4H-pyrano[3,2-d]-m-dioxin using 2-(1-hydroxyethyl)-3-hydroxy-pyran-4(1H)-one yielded the crude product. Purification by column chromatography on silica gel (eluant: EtOAc) furnished the title compound after recrystallisation from EtOAc/Pet. ether 40/60, as a white crystalline solid (yield=84.5%). m.p. 112–113 ° C.

$^1$H-NMR (CDCl$_3$) δ: 0.55 (d, 3H, CHCH$_3$), 5.0 (q, 1H, CHCH$_3$), 5.8 (s, 1H, CHPh), 6.25 (d, 1H, 7-H(pyranone)), 7.1–7.75 (m, 6H, Ar & 6-H(pyranone))

Anal. Calcd. for $C_{14}H_{12}O_4$: C, 68.85; H, 4.95%. Found: C, 68.63; H, 4.86%.

EXAMPLE 3

8-Oxo-4,8-dihydro-6-methyl-2-phenyl-4H-pyrano[3,2-d]-m-dioxin

In an analogous procedure in the preparation of 8-oxo-4,8-dihydro-2-phenyl-4H -pyrano[3,2-d]-m-dioxin using 2-hydroxymethyl-3-hydroxy-6-methyl-pyran-4(1H)-one afforded the title compound (Yield=82.1%) after recrystallisation from EtOAc/Pet. ether 40/60, as a white crystalline solid; m.p. 91–94° C.

$^1$H-NMR (CDCl$_3$) δ: 2.25 (s, 3H, 6-CH$_3$), 4.75 (d, 2H, CH$_2$O), 5.9 (s, 1H, CHPh 6.18 (s, 1 H, 7-H(pyranone)), 7.2–7.8 (m, 5H, Ar)

Anal. Calcd. for $C_{14}H_{12}O_4$: C, 68.85; H, 4.95%. Found: C, 68.63; H, 4.86%.

EXAMPLE 4

8-Oxo-4,8-dihydro-4,6-dimethyl-2-phenyl-4H-pyrano[3,2-d]-m-dioxin

In an analogous procedure in the preparation of 8-oxo-4,8-dihydro-2-phenyl-4H-pyrano[3,2-d]-m-dioxin using 2-(1-hydroxyethyl)-3-hydroxy-6-methyl-pyran-4(1H)-one yielded the crude product. Purification by column chromatography on silica gel (eluant: EtOAc) furnished the title compound after recrystallisation from EtOAc/Pet. ether 40/60, as a white crystalline solid (yield=86.7%). m.p. 120–122° C.

$^1$H-NMR (CDCl$_3$) δ: 1.6 (d, 3H, CHCH$_3$), 2.25 (s, 3H, 6-CH$_3$), 5.08 (q, 1H,CHCH$_3$), 5.9 (s, 1H, CHPh), 6.18 (s, 1H, 7-H(pyranone)), 7.2–7.8 (m, 5H, Ar)

Anal. Calcd. for $C_{15}H_{14}O_4$: C, 69.76; H, 5.46%. Found: C, 69.94; H, 5.67%.

EXAMPLE 5

8-Oxo-4,8-dihydro-4-ethyl-6-methyl-2-phenyl-4H-pyrano[3,2-d]-m-dioxin

In an analogous procedure in the preparation of 8-oxo-4,8-dihydro-2-phenyl-4H-pyrano[3,2-d]-m-dioxin using 2-(1-hydroxyproyl)-3-hydroxy-6-methyl-pyran-4(1H)-one afforded the title compound after recrystallisation from EtOAc/Pet. ether 40/60, as a white crystalline solid (Yield=61.3%); m.p. 111–114° C.

$^1$H-NMR (CDCl$_3$) δ: 1.0 (t, 3H, CHCH$_2$CH$_3$), 1.6–2.1 (m, 2H, CHCH$_2$CH$_3$), 2.2 (s, 3H, 6-CH$_3$), 4.7–5.0 (m, 1H, CHCH$_2$CH$_3$), 5.8 (s, 1H, CHPh), 6.1 (s, 1H, 7-H (pyranone)), 7.15–7.7 (m, 5H, Ar)

Anal. Calcd. for $C_{16}H_{16}O_4$: C, 70.58; H, 4.92%. Found: C, 70.35; H, 4.89%.

2-Hydroxymethyl-3-benzyloxy-6-methyl-pyran-4(1H)-one (known).

Sodium hydroxide (4.84 g, 121 mmol, 1.1 eq.) dissolved in 10 ml distilled water was added to 100 ml methanol containing 2-hydroxymethyl-3-hydroxy-6-methyl-pyran-4(1H)-one (17.2 g, 110 mmol, 1 eq.) and heated to reflux. Benzyl bromide (20.7 g, 121 mmol, 1 eq.) was added dropwise over 30 minutes and then refluxed overnight. The reaction mixture was concentrated in vacuo, the residue taken up into 300 ml dichloromethane and the inorganic salts filtered off. The dichloromethane layer was washed with 2×100 ml 5% w/v sodium hydroxide solution, 100 ml water, dried (Na$_2$SO$_4$), and concentrated in vacuo to yield the crude product as a yellow crystalline solid. Recrystallisation from $CH_2Cl_2$/Pet. ether 40/60 afforded the title product in 80% yield (21.6 g) as a white crystalline solid. m.p. 115–116° C. [lit. 114–116° C. Tilbrook (1995)].

$^1$H-NMR (CDCl$_3$) δ: 2.2 (s, 3H, 6-CH$_3$), 2.6 (br., s, 1H, 2-CH$_2$OH), 4.3 (br., s, 2H, 2-CH$_2$OH), 5.18 (s, 2H, CH$_2$Ph), 6.16 (s, 1H, 5-H(pyranone)), 7.4 (s, 5H, Ar)

Novel Intermediates and Orally Active Prodrugs of the Invention

EXAMPLE 6

2-(1-Hydroxyethyl)-3-benzyloxy-6-methyl-pyran-4(1H)-one

The title compound was prepared by the method outlined for 2-hydroxymethyl-3-benzyloxy-6-methyl-pyran-4(1H)-one, using 8.5 g (50 mmol, 1 eq.) of 2-(1-hydroxyethyl)-3-hydroxy-6-methyl-pyran-4(1H)-one and 9.5 g benzyl bromide (55 mmol, 1.1 eq.) to yield the pure product 10.1 g (77.7%) after recrystallisation from $CH_2Cl_2$/Pet. ether 40/60, as a white crystalline solid. m.p 91–92° C.

$^1$H-NMR (CDCl$_3$) δ: 1.25 (d, 3H, 2-CHCH$_3$), 2.25 (s, 3H, 6-CH$_3$), 2.55 (br., s, 1H, 2-CHOH), 4.9 (q, 1H, 2-CHCH$_3$), 5.18 (s, 2H, CH$_2$Ph), 6.16 (s, 1H, 5-H (pyranone)), 7.4 (s, 5H, Ar)

EXAMPLE 7

2-(1'-Hydroxypropyl)-3-benzyloxy-6-methyl-pyran-4(1H)-one

The title compound was prepared by the method outlined for 2-hydroxymethyl-3-benzyloxy-6-methyl-pyran-4(1H)- one, using 7.36 g (40 mmol, 1 eq.) of 2-(1-hydroxypropyl)-3-hydroxy-6methyl-pyran-4(1H)-one and 7.5 g benzyl bromide (44 mmol, 1.1 eq.) to yield the pure product 8.9 g (81.2%) after recrystallisation from $CH_2Cl_2$/Pet. ether 40/60, as a white crystalline solid. m.p. 88–89° C.

$^1$H-NMR (CDCl$_3$) δ: 0.8 (t, 3H, 2-CHCH$_2$CH$_3$), 1.2–1.9 (m, 2H, 2-CHCH$_2$CH$_3$), 2.2 (s, 3H, 6-CH$_3$), 2.4 (br., s, 1H, 2-CHOH), 4.5 (t, 1H, 2-CHCH$_2$CH$_3$), 5.08 (s, 2H, CH$_2$Ph), 6.04 (s, 1H, 5-H(pyranone)), 7.28 (s, 5H, Ar)

2-Hydroxymethyl-3-benzyloxy-pyran-4(1H)-one (known)

The title compound was prepared by the method outlined for 2-hydroxymethyl-3-benzyloxy-6-methyl-pyran-4(1B)-one, using 7.1 g (50 mmol, 1 eq.) of 2-hydroxymethyl-3-hydroxy-pyran-4(1 H)-one and 9.5 g benzyl bromide (55 mmol, 1.1 eq.) to yield the crude product as an organe oil. Further purification by column chromatography on silica gel (eluant: 10% CH$_3$OH/90% CHCl$_3$) furnished the pure product (9.4 g, 81%) as a bright yellow oil. (Looker and Clifton (1986).

$^1$H-NMR (CDCl$_3$) δ: 1.8 (br., s, 1H, 2-CH$_2$OH), 4.4 (br., s, 2H, 2-CH$_2$OH), 5.18 (s, 2H, CH$_2$Ph), 6.35 (d, 1H, 5-H(pyranone)), 7.4 (s, 5H, Ar), 7.65 (d, 1H, 6-H(pyranone))

EXAMPLE 8

2-(1'-Hydroxyethyl)-3-benzyloxy-pyran-4(1H)-one

The title compound was prepared by the method outlined for 2-hydroxymethyl-3-benzyloxy-6-methyl-pyran-4(1H)-one, using 4.68 g (30 mmol, 1 eq.) of 2-(1-hydroxyethyl)-3-hydroxy-pyran-4(1H)-one and 5.64 g benzyl bromide (33 mmol, 1.1 eq.) to yield the pure product 6.1 g (82%) after recrystallisation from $CH_2Cl_2$/Pet. ether 40/60, as a white crystalline solid. m.p. 97–100° C.

$^1$H-NMR (CDCl$_3$) δ: 1.35 (d, 3H, 2-CHCH$_3$), 2.5 (br., s, 1H, 2-CHOH), 4.95 (q, 1H, 2-CHCH$_3$), 5.21 (s, 2H, CH$_2$Ph), 6.38 (d, 1H, 5-H(pyranone)), 7.4 (s, 5H, Ar), 7.7 (d, 1H, 6-H(pyranone))

Orally Active Prodrugs of the Invention

EXAMPLE 9

2-Methoxymethyl-3-benzyloxy-6-methyl-pyran-4(1H)-one

To a suspension of sodium hydride (0.48 g, 20 mmol, 2 eq.) in 30 ml dry DMF was added 2-hydroxymethyl-3-benzyloxy-6-methyl-pyran-4(1H)-one (2.46 g, 10 mmol, 1 eq.) followed by dropwise addition of iodomethane (4.26 g, 30 mmol, 3 eq.) at 0° C. under nitrogen. After stirring for 30 minutes at this temperature, the reaction mixture was poured into ice cold water (100 ml) and extracted with dichloromethane (3×50 ml). The combined organic fractions were dried over anhydrous sodium sulphate, filtered and concentrated in vacuo to yield the crude product (2.6 g,~100%) as an orange oil which solidified on cooling. Recrystallisation from $CH_2Cl_2$/Pet. ether 40/60 afforded the pure product (2.35 g, 90%) as a white crystalline solid. m.p. 30–32° C.

$^1$H-NMR (CDCl$_3$) δ: 2.25 (s, 3H, 6-CH$_3$), 3.26 (s, 3H, OCH$_3$), 4.2 (s, 2H, 2-CH$_2$OCH$_3$), 5.18 (s, 2H, CH$_2$Ph), 6.16 (s, 1H, 5-H(pyranone)), 7.35 (s, 5H, Ar)

EXAMPLE 10

2-(1-Methoxyethyl)-3-benzyloxy-6-methyl-pyran-4(1H)-one

In an analogous procedure in the preparation of 2-methoxymethyl-3-benzyloxy-6-methyl-pyran-4(1 H)-one using 2-(1-hydroxyethyl)-3-benzyloxy-6-methyl-pyran-4(1 H)-one (2.6 g, 10 mmol, 1 eq.) yielded the title compound as an orange oil (2.65 g, 97%). Further purification by column chromatography on silica gel (eluant: EtOAc) furnished the pure product as a bright yellow oil.

$^1$H-NMR (CDCl$_3$) δ: 1.18 (d, 3H, 2-CHCH$_3$), 2.25 (s, 3H, 6-CH$_3$), 3.1 (s, 3OCH$_3$), 4.5 (q, 1H, 2-CHCH$_3$), 5.2 (s, 2H, CH$_2$Ph), 6.16 (s, 1H, 5-H(pyranone)), 7.4 (s, 5H, Ar).

EXAMPLE 11

2-(1'-Methoxypropyl)-3-benzyloxy-6-methyl-pyran-4(1H)-one

In an analogous procedure in the preparation of 2-methoxymethyl-3-benzyloxy-6-methyl-pyran-4(1H)-one using 2-(1-hydroxypropyl)-3-benzyloxy-6-methyl-pyran-4(1H)-one (5.48 g, 20 mmol, 1 eq.) yielded the title compound (5.2 g, 90.3%) as an orange oil which solidified on cooling. Recrystallisation from $CH_2Cl_2$/Pet. ether 40/60 afforded the pure product as a white crystalline solid. m.p. 63–65 ° C.

$^1$H-NMR (CDCl$_3$) δ: 0.9 (t, 3H, 2-CHCH$_2$CH$_3$), 1.2–1.8 (m, 2H, 2-CHCH$_2$CH$_3$), 2.34 (s, 3H, 6-CH$_3$), 3.18 (s, 3H OCH$_3$), 4.3 (t, 1H, 2-CHCH$_2$CH$_3$), 5.24 (s, 2H, CH$_2$Ph), 6.2 (s, 1H, 5-H(pyranone)), 7.38 (s, 5H, Ar)

EXAMPLE 12

2-Methoxymethyl-3-benzyloxy-pyran-4(1H)-one

In an analogous procedure in the preparation of 2-methoxymethyl-3-benzyloxy-6-methyl-pyran-4(1H)-one using 2-hydroxymethyl-3-benzyloxy-pyran-4(1H)-one (2.32 g, 10 mmol, 1 eq.) yielded the title compound as an orange oil (2.5 g, ~100%). Further purification by column chromatography on silica gel (eluant: EtOAc) furnished the pure product as a bright yellow oil.

$^1$H-NMR (CDCl$_3$) δ: 3.25 (s, 3H, OCH$_3$), 4.3 (s, 2H, 2-CH$_2$OCH$_3$), 5.2 (s, 2H,CH$_2$Ph), 6.3 (d, 1H, 5-H (pyranone)), 7.3 (s, 5H, Ar), 7.65 (d, 1H, 6-H (pyranone))

EXAMPLE 13

2-(1-Methoxyethyl)-3-benzyloxy-pyran-4(1H)-one

In an analogous procedure in the preparation of 2-methoxymethyl-3-benzyloxy-6-methyl-pyran-4(1H)-one using 2-(1-hydroxyethyl)-3-benzyloxy-pyran-4(1H)-one (2.46 g, 10 mmol, 1 eq.) yielded the title compound as a yellow oil (2.4 g, 92.3%). Further purification by column chromatography on silica gel (eluant: EtOAc) furnished the pure product (2.1 g, 80.8%) as a bright yellow oil.

$^1$H-NMR (CDCl$_3$) δ: 1.18 (d, 3H, 2-CHCH$_3$), 3.1 (s, 3H, OCH$_3$), 4.45 (q, 1H, 2-CHCH$_3$), 5.2 (s, 2H, CH$_2$Ph), 6.3 (d, 1H, 5-H(pyranone)), 7.3 (s, 5H, Ar), 7.65 (d, 1H, 6-H (pyranone))

EXAMPLE 14

2-(1-Ethoxyethyl)-3-benzyloxy-6-methyl-pyran-4(1H)-one

In an analogous procedure in the preparation of 2-methoxymethyl-3-benzyloxy-6-methyl-pyran-4(1H)-one using 2-(1-hydroxyethyl)-3-benzyloxy-6-methyl-pyran-4(1 H)-one (5.2 g, 20 mmol, 1 eq.) and 9.36 g iodoethane (60 mmol, 3 eq.) yielded the title compound as an orange oil (5.4 g, 94% Crude). Further purification by column chromatography on silica gel (eluant: EtOAc) furnished the pure product as a bright yellow oil.

$^{1}$H-NMR (CDCl$_{3}$) δ: 1.05–1.65 (m, 6H, 2-CHCH$_{3}$ & OCH$_{2}$CH$_{3}$), 2.38 (s, 3H, 6-CH$_{3}$), 3.3 (q, 2H, OCH$_{2}$CH$_{3}$), 4.65 (q, 1H, 2-CHCH$_{3}$), 5.25 (s, 2H, CH$_{2}$Ph), 6.2 (s, 1H, 5-H(pyranone)), 7.4 (s, 5H, Ar)

Novel Intermediates of the Invention

EXAMPLE 15

8-Oxo-4,8-dihydro-2-phenyl-5-methyl-4H-pyridino [3,2-d]-m-dioxin

To a solution of 8-oxo-4,8-dihydro-2-phenyl-4H-pyrano [3,2-d]-m-dioxin (2.3 g, 10 mmol, 1 eq.) in ethanol (10 ml)/water (10 ml) was added 2.5 ml (20 mmol, 2 eq.) of 40% aqueous methylamine followed by 2N sodium hydroxide solution until pH 12.5 was obtained. The reaction mixture was sealed in a thick-walled glass tube and stirred at 70° C. for 3 hours. After adjustment to pH 1 with concentrated hydrochloric acid, the solvent was removed by rotary evaporation prior to addition of water (50 ml) and washing with diethyl ether (3×50 ml). Subsequent adjustment of the aqueous fraction to pH 7 with 10N sodium hydroxide solution was followed by extraction into dichloromethane (4×50 ml), the combined organic layers then being dried over anhydrous sodium sulphate, filtered, rotary evaporated to give a yellow solid. Recrystallisation from methanol/ diethyl ether afforded the pure product (1.6 g, 65.8%) as a light yellow crystalline solid. m.p. 210–211° C.

$^{1}$H-NMR (DMSO-d$_{6}$) δ: 3.55 (s, 3H, N—CH$_{3}$), 5.08 (s, 2H, CH$_{2}$O), 5.92 (s, 1H, CHPh), 6.12 (d, 1H, 7-H (pyridinone)), 7.25–7.85 (m, 6H, Ar & 6-H(pyridinone))

EXAMPLE 16

8-Oxo-4,8-dihydro-2-phenyl-5,6-dimethyl-4H-pyridino[3,2-d]-m-dioxin

In an analogous procedure in the preparation of 8-oxo-4, 8-dihydro-2-phenyl-5-methyl-4H-pyridino[3,2-d]-m-dioxin using 8-oxo-4,8-dihydro-6-methyl-2-phenyl-4H-pyrano[3, 2-d]-m-Dioxin (1.22 g, 5 mmol) yielded the title compound as a white powder (0.85 g, 66%). m.p. 256–258° C.

1H-NMR (methanol-d$_{4}$) δ: 2.2 (s, 3H, 6-CH$_{3}$), 3.35 (s, 3H, N—CH$_{3}$), 4.95 (s, 2H, CH$_{2}$O), 5.8 (s, 1H, CHPh), 6.5 (s, 1H, 7-H(pyridinone)), 7.0–7.5 (m, 5H, Ar)

EXAMPLE 17

8-Oxo-4,8-dihydro-2-phenyl-4,5,6-trimethyl-4H-pyridino[3,2-d]-m-dioxin

In an analogous procedure in the preparation of 8-oxo-4, 8-dihydro-2-phenyl-5-methyl-4H-pyridino[3,2-d]-m-dioxin using 8-oxo-4,8-dihydro-4,6-dimethyl-2-phenyl-4H-pyrano-[3,2-d]-m-dioxin (2.58 g, 10 mmol) yielded the crude product Further purification by column chromatography on silica gel (eluant: 20% CH$_{3}$OH/80% CHC$_{3}$) afforded the pure title compound (1.54 g, 56.8%) after recrystallisation from methanol/diethyl ether as a pale yellow crystalline solid. m.p. 199–201° C.

$^{1}$H-NMR (DMSO-d$_{6}$) δ: 1.7 (dd, 3H, CHCH$_{3}$), 2.35 (s, 3H, 6-CH$_{3}$), [3.44 (s, isomer B) & 3.5 (s, isomer A); 3H, N—CH$_{3}$], 4.9–5.4 (m, 1H, CHCH$_{3}$), [5.75 (s, isomer A) & 6.05 (s, isomer B); 1H, CHPh], 6.35 (s, 1H, 7-H (pyridinone)), 7.2–7.9 (m, 5H, Ar)

EXAMPLE 18

8-Oxo-4,8 dihydro-2-phenyl-4-ethyl-5,6dimethyl-4H-pyridino[3,2-d]-m-dioxin

In an analogous procedure in the preparation of 8-oxo-4, 8-dihydro-2-phenyl-5-methyl-4H-pyridino[3,2-d]-m-dioxin using 8-oxo-4,8-dihydro-4-ethyl-6-methyl-2-phenyl-4H-pyrano-[3,2-d]-m-dioxin (4.08 g, 15 mmol) yielded the crude product. Further purification by column chromatography on silica gel (eluant: 20% CH$_{3}$OH/80% CHCl$_{3}$) afforded the pure title compound (1.7 g, 39.8%) after recrystallisation from CHCl$_{3}$/diethyl ether as a pale yellow crystalline solid. m.p. 185–187° C.

$^{1}$H-NMR (DMSO-d$_{6}$) δ: 0.8–1.4 (m, 3H, CHCH$_{2}$CH$_{3}$), 1.5–2.2 (m, 2H, CHCH$_{2}$CH$_{3}$) 2.3 (s, 3H, 6-CH$_{3}$), [3.38 (s, isomer B) & 3.45 (s, isomer A); 3H, N—CH$_{3}$], [4.5–4.8 (m, isomer B) & 4.9–5.4 (m, isomer A); 1H, CHCH$_{2}$CH$_{3}$], [5.68 (s, isomer A) & 5.95 (s, isomer B); 1H, CHPh], 6.25 (s, 1H, 7-H (pyridinone)), 7.2–7.8 (m, 5H, Ar)

EXAMPLE 19

8-Oxo-4,8-dihydro-2-phenyl-4-methyl-5-ethyl-4H-pyridino[3,2-d]-m-dioxin

To a solution of 8-oxo-4,8-dihydro-4-methyl-2-phenyl-4H-pyrano[3,2-d]-m-dioxin (1.7 g, 7 mmol, 1 eq.) in ethanol (10 ml)/water (10 ml) was added 1.2 ml (14 mmol, 2 eq.) of 70% aqueous ethylamine followed by 2N sodium hydroxide solution until pH 12.5 was obtained. The reaction mixture was sealed in a thick-walled glass tube and stirred at 70° C. for 3 hours. After removal the solvent, the residue was purified by column chromatography on silica gel (eluant: 15% CH$_{3}$OH/85% CHCl$_{3}$) to afford the title product (1.5 g, 79.1%) as a yellow oil.

$^{1}$H-NMR (CDCl$_{3}$) δ: 1.2–2.2 (m, 6H, CHCH$_{3}$ & N—CH$_{2}$CH$_{3}$), 3.4–4.0 (m, 2H, N—CH$_{2}$CH$_{3}$), 4.8–5.4 (m, 1H, CHCH$_{3}$), [5.6 (s, isomer A) & 6.0 (s, isomer B); 1H, CHPh], 6.3 (d, 1H, 7-H(pyridinone)), 7.0–7.7 (m, 6H, Ar & 6-H(pyridinone)).

EXAMPLE 20

8-Oxo-4,8-dihydro-2-phenyl-5(3-hydroxypropyl)4H-pyridino[3,2-d]-m-dioxin

To a solution of 8-oxo-4,8-dihydro-2-phenyl-4H-pyrano [3,2-d]-m-dioxin (3.45 g, 15 mmol, 1 eq.) in ethanol (50 ml)/water (50 ml) was added 3-hydroxypropylamine (2.25 g, 30 mmol, 2 eq.) followed by 2N sodium hydroxide solution until pH 12.5 was obtained. The reaction mixture was refluxed for 3 hours. TLC analysis (10% CH$_{3}$OH/90% CHCl$_{3}$) showed that no starting material was present. After removal of solvent by rotary evaporation, the residue was purified by column chromatography on silica gel (eluant: 20% CH$_{3}$OH/80% CHCl$_{3}$) to afford the title compound (3.35 g, 77.8%) as a yellow crystalline solid m.p. 73–76° C.

$^{1}$H-NMR (CDCl$_{3}$) δ: 1.5–2.1 (m, 2H, N—CH$_{2}$CH$_{2}$CH$_{2}$O), 3.2–4.0 (m, 4H, N—CH$_{2}$CH$_{2}$CH$_{2}$O), 4.0–5.2 (br., 1H, OH), 4.8 (s, 2H, CH$_{2}$O), 5.7 (s, 1H, CHPh), 6.2 (d, 1H, 7-H(pyridinone)), 7.0–7.8 (m, 6H, Ar & 6-H (pyridinone))

EXAMPLE 21

8-Oxo-4,8-dihydro-2-phenyl-4-methyl-5-(3-hydroxypropyl)-4H-pyridino [3,2-d]-m-dioxin In an analogous procedure in the preparation of 8-oxo-4, 8-dihydro-2-phenyl-5-(3-hydroxypropyl)4H-pyridino[3,2-d]-m-dioxin using 8-oxo-4,8-dihydro-4methyl-2-phenyl-4H-pyrano[3,2-d]-m-dioxin (1.83 g, 7.5 mmol, 1 eq.) yielded the title compound (1.3 g, 57.6%) after purification by column chromatography on silica gel (eluant: 20% CH$_{3}$OH/80% CHCl$_{3}$) as a yellow oil.

$^1$H-NMR (CDCl$_3$) δ: 1.5 (d, 3H, CHCH$_3$), 1.5–2.1 (m, 2H, N—CH$_2$CH$_2$CH$_2$O), 3.2–4.0 (m, 4H, N—CH$_2$CH$_2$CH$_2$O), 4.0–5.2 (br., 1H, OH), 5.28 (q, 1H, CHCH$_3$), 5.58 (s, 1H, CHPh), 6.2 (d, 1H, 7-H(pyridinone)), 7.0–7.8 (m, 6H, Ar & 6-H (pyridinone))

EXAMPLE 22

8-Oxo-4,8-dihydro-2-phenyl-5-[(3-benzoyloxy) propyl]-4H-pyridino [3,2-d]-m-dioxin A solution of triphenyl phosphine (3.46 g, 13.2 mmol, 1.1 eq.) and 8-oxo-4,8-dihydro-2-phenyl-5-(3-hydroxypropyl) 4H-pyridino[3,2-d]-m-dioxin (3.3 g, 12 mmol, 1 eq.) in dry tetrahydrofuran (100 ml) was added dropwise to a solution of diethyl azodicarboxylate (2.3 g, 13.2 mmol, 1.1 eq.) and benzoic acid (1.5 g, 12 mmol, 1 eq.) in dry tetrahydrofuran (30 ml) at room temperature. After stirring the mixture overnight at room temperature, the solvent was removed under reduced pressure. The residue thus obtained was purified by column chromatography on silica gel (eluant: 12% CH$_3$OH/88% CHCl$_3$) to afford the title compound (4.1 g, 89.7%) as a light yellow oil.

$^1$H-NMR (CDCl$_3$) δ: 1.95–2.55 (m, 2H, N—CH$_2$CH$_2$CH$_2$O), 3.82 (t, 2H, N—CH$_2$CH$_2$CH$_2$O), 4.34 (t, 2H, N—CH$_2$CH$_2$CH$_2$O), 4.9 (s, 2H, CH$_2$O), 5.8 (s, 1H, CHPh), 6.3 (d, 1H, 7-H(pyridinone)), 7.0–8.2 (m, 11H, Ar & 6-H (pyridinone)).

Orally Active Prodrugs of the Invention

EXAMPLE 23

1,6-Dimethyl-2-methoxymethyl-3-benzyloxy-pyridin-4(1H)-one hydrochloride

To a solution of 2-methoxymethyl-3-benzyloxy-6-methyl-pyran-4(1 H)-one (3.12 g, 12 mmol, 1 eq.) in ethanol (10 ml)/water (10 ml) was added 2.8 g (36 mmol, 3 eq.) of 40% aqueous methylamine followed by 2N sodium hydroxide solution until pH 13 was obtained. The reaction mixture was sealed in a thick-walled glass tube and stirred at 70° C. for 12 hours. After adjustment to pH 1 with concentrated hydrochloric acid, the solvent was removed by rotary evaporation prior to addition of water (50 ml) and washing with diethyl ether (3×50 ml). Subsequent adjustment of the aqueous fraction to pH 7 with 10N sodium hydroxide solution was followed by extraction into dichloromethane (4×50 ml), the combined organic layers then being dried over anhydrous sodium sulphate, filtered and the solvent removed in vacuo. The residue was redissolved in 30 ml methanol and adjusted to pH 1 with concentrated hydrochloric acid. The solution was reconcentrated in vacuo to yield the crude product. Recrystallization from methanol/diethyl ether gave the pure title compound (3.05 g, 82%) as a white crystalline solid m.p. 125–128° C.

$^1$H-NMR (DMSO-d$_6$) δ: 2.6 (s, 3H, 6-CH$_3$), 3.26 (s, 3H, OCH$_3$), 3.86 (s, 3H, N—CH$_3$), 4.6 (s, 2H, 2-CH$_2$OCH$_3$), 5.04 (s, 2H, CH$_2$Ph), 5.5–6.5 (br., 1H, OH), 7.2–7.8 (m, 6H, Ar & 5-H(pyridinone))

EXAMPLE 24

1,6-Dimethyl-2-(1-methoxyethyl)-3-benzyloxy-pyridin-4(H)-one hydrochloride

The title compound was prepared by the method outlined for 1,6-dimethyl-2-methoxy-methyl-3-benzyloxy-pyridin-4 (1H)-one hydrochloride, using 3.56 g (13 mmol, 1 eq.) of 2-(1-methoxyethyl)-3-benzyloxy-6-methyl-pyran-4(1H)-one to yield the pure product 2.64 g (62.8%) after recrystallisation from methanol/diethyl ether, as a white crystalline solid m.p. 117–119° C.

$^1$H-NMR (DMSO-d$_6$) δ: 1.3 (d, 3H, CHCH$_3$), 2.54 (s, 3H, 6-CH$_3$), 3.04 (s, 3H, OCH$_3$), 3.96 (s, 3H, N—CH$_3$), 5.08 (s, 2H, CH$_2$Ph), 5.12 (q, 1H, CHCH$_3$), 7.4 (s, 5H, Ar), 7.6 (s, 1H, 5-H(pyridinone))

EXAMPLE 25

1-Ethyl-2-methoxymethyl-3-benzyloxy-6-methyl-pyridin-4(1H)-one hydrochloride

The title compound was prepared by the method outlined for 1,6-dimethyl-2-methoxy-methyl-3-benzyloxy-pyridin-4 (1H)-one hydrochloride, using 6.5 g (25 mmol, 1 eq.) of 2-(1-methoxymethyl)-3-benzyloxy-6-methyl-pyran-4(1H)-one and 4.82 g (75 mmol, 3 eq.) of 70% aqueous ethylamine to yield the pure product 3.7 g (45.7%) after recrystallisation from methanol/diethyl ether, as a white crystalline solid m.p. 114–116° C.

$^1$H-NMR (DMSO-d$_6$) δ: 1.3 (t, 3H, N—CH$_2$CH$_3$), 2.64 (s, 3H, 6-CH$_3$), 3.27 (s, 3H, OCH$_3$), 4.35 (q, 2H, N—CH$_2$CH$_3$), 4.6 (s, 2H, 2-CH$_2$OCH$_3$) 5.1 (s, 2H, CH$_2$Ph), 6.0–7.0 (br., 1H, OH), 7.45 (s, 5H, Ar), 7.52 (s, 1H, 5-H(pyridinone))

EXAMPLE 26

1-Ethyl-2-methoxymethyl-3-benzyloxy-pyridin-4 (1H)-one

To a solution of 2-methoxymethyl-3-benzyloxy-pyran-4 (1H)-one (2.46 g, 10 mmol, 1 eq.) in ethanol (10 ml)/water (10 ml) was added 1.93 g (30 mmol, 3 eq.) of 70% aqueous ethylamine followed by 2N sodium hydroxide solution until pH 13 was obtained. The reaction mixture was sealed in a thick-walled glass tube and stirred at 70° C. overnight. After adjustment to pH 1 with concentrated hydrochloric acid, the solvent was removed by rotary evaporation prior to addition of water (50 ml) and washing with diethyl ether (3×50 ml). Subsequent adjustment of the aqueous fraction to pH 7 with 10N sodium hydroxide solution was followed by extraction into dichloromethane (4×50 ml), the combined organic layers then being dried over anhydrous sodium sulphate, filtered and the solvent removed in vacuo. The residue was purified by column chromatography on silica gel (eluant: 15% CH$_3$OH/85% CHCl$_3$) to afford the title compound (2.05 g, 75.1 %) as a yellow oil.

$^1$H-NMR (CDCl$_3$) δ: 1.3 (t, 3H, N—CH$_2$CH$_3$), 3.24 (s, 3H, OCH$_3$), 3.95 (q, 2H, N—CH$_2$CH$_3$), 4.35 (s, 2H, 2-CH$_2$OCH$_3$), 5.25 (s, 2H, CH$_2$Ph), 6.45 (d, 1H, 5-H (pyridinone)), 7.15–7.6 (m, 6H, Ar & 5-H(pyridinone)).

EXAMPLE 27

1-Ethyl-2-(1-methoxyethyl)-3-benzyloxy-pyridin-4 (1H)-one

In an analogous procedure in the preparation of 1-ethyl-2-methoxymethyl-3-benzyloxy-pyridin-4(1H)-one using 2-(1-methoxyethyl)-3-benzyloxy-pyran-4(1H)-one 3.12 g (12 mmol, 1 eq.) yielded the title compound (1.03 g, 29.6%) after purification by column chromatography on silica gel (eluant: 15% CH$_3$OH/85% CHCl$_3$) as a yellow oil.

$^1$H-NMR (CDCl$_3$) δ: 1.1–1.6 (m, 6H, CHCH$_3$ & N—CH$_2$CH$_3$), 3.0 (s, 3H, OCH$_3$), 4.1 (q, 2H, N—CH$_2$CH$_3$), 4.95 (q, 1H, CHCH$_3$), 5.18 (s, 2H, CH$_2$Ph), 6.3 (d, 1 H, 5-H (pyridinone)), 7.0–7.5 (m, 6H, Ar & 5-H(pyridinone))

EXAMPLE 28

1,6-Dimethyl-2-(1-methoxypropyl)-3-benzyloxy-pyridin-4(1H)-one

In an analogous procedure in the preparation of 1-ethyl-2-methoxymethyl-3-benzyloxy-pyridin-4(1H)-one using 2-(1-methoxypropyl)-3-benzyloxy-6-methyl-pyran-4(1H)-one 4.32 g (15 mmol, 1 eq.) and 3.49 g (45 mmol, 3 eq.) of 40% aqueous methylamine yielded the title compound (1.7 g, 37.6%) after purification by column chromatography on silica gel (eluant: 15% $CH_3OH$/85% $CHCl_3$) as a yellow oil.

$^1$H-NMR ($CDCl_3$) δ: 0.9 (t, 3H, $CHCH_2CH_3$), 1.1–1.9 (m, 2H, $CHCH_2CH_3$), 2.3 (s, 3H, 6-$CH_3$), 3.05 (s, 3H, $OCH_3$), 3.65 (s, 3H, N—$CH_3$), 4.65–5.0 (m, 1H, $CHCH_2CH_3$), 5.24 (s, 2H, $CH_2Ph$), 6.3 (d, 1H, 5-H (pyridinone)), 7.1–7.6 (m, 6H, Ar)

EXAMPLE 29

1,6-Dimethyl-2-(1-ethoxymethyl)-3-benzyloxy-pyridin-4(1H)-one

In an analogous procedure in the preparation of 1-ethyl-2-methoxymethyl-3-benzyloxy-pyridin-4(1H)-one using 2-(1-ethoxymethyl)-3-benzyloxy-6-methyl-pyran-4(1H)-one 5.76 g (20 mmol, 1 eq.) and 4.65 g (60 mmol, 3 eq.) of 40% aqueous methylamine yielded the title compound (3.68 g, 61.1%) after purification by column chromatography on silica gel (eluant: 15% $CH_3OH$/85% $CHCl_3$) as a yellow oil.

$^1$H-NMR ($CDCl_3$) δ: 1.1–1.6 (m, 6H, $CHCH_3$ & $OCH_2CH_3$), 2.3 (s, 3H, 6-$CH_3$), 3.2 (q, 2H, $OCH_2CH_3$), 3.7 (s, 3H, N—$CH_3$), 5.2 (q, 1H, $CHCH_3$), 5.25 (s, 2H, $CH_2Ph$), 6.3 (s, 1H, 5-H(pyridinone)), 7.1–7.6 (m, 5H, Ar)

De-Alkylated Active Metabolites of Orally Active Compounds of the Invention

EXAMPLE 30

1-Methyl-2-hydroxymethyl-3-hydroxy-pyridin-4(1H)-one hydrochloride

8-Oxo-4,8-dihydro-2-phenyl-5-methyl-4H-pyridino[3,2-d]-m-dioxin (1.22 g, 5 mmol) was dissolved in 30 ml of ethanol and adjusted to pH 1 with concentrated hydrochloric acid prior to hydrogenolysis for 12 hours in the presence of 5% Pd/C catalyst (0.2 g). Filtration followed by rotary evaporation gave the crude product as a white solid. Recrystallization from methanol/diethyl ether gave the pure title compound (0.82 g, 86%) as a white crystalline solid. m.p. 157–159° C.

$^1$H-NMR (DMSO-$d_6$) δ: 4.18 (s, 3H, N—$CH_3$), 4.8 (s, 2H, 2-$CH_2OH$), 7.4 (d, 1H, 5-H(pyridinone)), 8.3 (d, 1H, 6-H(pyridinone)), 7.6–9.3 (br., 3H, OH)

Anal. Calcd. for $C_7H_{10}NO_3Cl$: C, 43.88; H, 5.26; N, 7.31%. Found: C, 44.14; H, 5.34; N, 7.28%.

EXAMPLE 31

1,6-Dimethyl-2-hydroxymethyl-3-hydroxy-pyridin-4(1H)-one hydrochloride

In an analogous hydrogenation procedure in the preparation of 1-methyl-2-hydroxymethyl-3-hydroxy-pyridin-4(1H)-one hydrochloride, using 8-oxo-4,8-dihydro-2-phenyl-5,6-dimethyl-4H-pyridino[3,2-d]-m-dioxin (0.64 g, 2.5 mmol) and 5% Pd/C catalyst (0.1 g) yield the title compound 0.45 g (87.5%) after recrystallisation from methanol/diethyl ether, as a white crystalline solid. m.p. 140–143° C.

$^1$H-NMR (DMSO-$d_6$) δ: 2.7 (s, 3H, 6-$CH_3$), 4.06 (s, 3H, N—$CH_3$), 4.86 (s, 2H, 2-$CH_2OH$), 7.4 (s, 1H, 5-H (pyridinone)), 6.4–8.7 (br., 3H, OH)

Anal. Calcd. for $C_8H_{12}NO_3Cl.½H_2O$: C, 44.77; H, 6.10; N, 6.53%. Found: C, 44.72; H, 6.00; N, 6.26%.

EXAMPLE 32

1,6-Dimethyl-2-(1-hydroxyethyl)-3-hydroxy-pyridin-4(1H)-one hydrochloride

In an analogous hydrogenation procedure in the preparation of 1-methyl-2-hydroxymethyl-3-hydroxy-pyridin-4(1H)-one hydrochloride, using 8-oxo-4,8-dihydro-2-phenyl-4,5,6-trimethyl-4H-pyridino[3,2-d]-m-dioxin (1.36 g, 5 mmol) and 5% Pd/C catalyst (0.3 g) yield the title compound 0.9 g (82%) after recrystallisation from methanol/diethyl ether, as a light yellow crystalline solid. m.p. 208–212° C.

$^1$H-NMR (DMSO-$d_6$) δ: 1.4 (d, 3H, $CHCH_3$),;2.5 (s, 3H, 6-$CH_3$), 4.04 (s, 3H, N—$CH_3$), 5.65 (q, 1H, $CHCH_3$), 7.3 (s, 1H, 5-H(pyridinone)), 7.5–10.0 (br., 3H, OH)

Anal. Calcd. for $C_9H_{14}NO_3Cl$: C, 49.21; H, 6.42; N, 6.38%. Found: C, 49.12; H, 6.33; N, 6.22%.

EXAMPLE 33

1,6-Dimethyl-2-(1-hydroxypropyl)-3-hydroxy-pyridin-4(1H)-one hydrochloride

In an analogous hydrogenation procedure in the preparation of 1-methyl-2-hydroxymethyl-3-hydroxy-pyridin-4(1H)-one hydrochloride, using 8-oxo-4,8-dihydro-2-phenyl-4-ethyl-5,6-dimethyl4H-pyridino[3,2-d]-m-dioxin (1.43 g, 5 mmol) and 5% Pd/C catalyst (0.3 g) yield the title compound 0.93 g (79.7%) after recrystallisation from methanol/diethyl ether, as a white crystalline solid. m.p. 221–223° C.

$^1$H-NMR (DMSO-$d_6$) δ: 0.8 (t, 3H, $CHCH_2CH_3$), 1.3–2.1 (m, 2H, $CHCH_2CH_3$), 2.43 (s, 3H, 6-$CH_3$), 3.94 (s, 3H, N—$CH_3$), 5.3 (t, 1H, $CHCH_2CH_3$), 7.15 (s, 1H, 5-H (pyridinone)), 7.5–10.5 (br., 3H, OH)

Anal. Calcd. for $C_{10}H_{16}NO_3Cl$: C, 51.40; H, 6.90; N, 5.99%. Found: C, 51.45; H, 6.82; N, 5.89%.

EXAMPLE 34

1-Ethyl-2-(1-hydroxyethyl)-3-hydroxy-pyridin-4(1H)-one hydrochloride

In an analogous hydrogenation procedure in the preparation of 1-methyl-2-hydroxymethyl-3-hydroxy-pyridin-4(1H)-one hydrochloride, using 8-oxo-4,8-dihydro-2-phenyl-4-methyl-5-ethyl-4H-pyridino[3,2-d]-m-dioxin (1.5 g, 5.5 mmol) and 5% Pd/C catalyst (0.3 g) yield the title compound 1.0 g (82.8%) after recrystallisation from methanol/diethyl ether, as a white crystalline solid. m.p. 139–140° C.

$^1$H-NMR (DMSO-d6) δ: 1.3–1.9 (m, 6H, $CHCH_3$ & N—$CH_2CH_3$, 4.6 (q, 2H, N—$CH_2CH_3$), 5.55 (q, 1H, $CHCH_3$), 7.4 (d, 1H, 5-H(pyridinone)), 8.25 (d, 1H, 5-H (pyridinone)), 8.5–10.5 (br., 3H, OH)

Anal. Calcd. for $C_9H_{14}NO_3Cl$: C, 49.21; H, 6.42; N, 6.38%. Found: C, 49.30; H, 6.44; N, 6.30%.

EXAMPLE 35

1-(3-hydroxypropyl)-2-hydroxymethyl-3-hydroxy-pyridin-4(1H)-one hydrochloride In an analogous hydrogenation procedure in the preparation of 1-methyl-2-hydroxymethyl-3-hydroxy-pyridin-4

(1H)-one hydrochloride, using 8-oxo-4,8-dihydro-2-phenyl-5-(3-hydroxypropyl)-4H-pyridino[3,2-d]-m-dioxin (1.44 g, 5 mmol) and 5% Pd/C catalyst (0.3 g) yield the title compound 0.98 g (83.2%) after recrystallisation from methanol/diethyl ether, as a white crystalline solid. m.p. 138–139° C.

$^1$H-NMR (D$_2$O) δ: 1.9–2.6 (m, 2H, N—CH$_2$CH$_2$CH$_2$O), 3.75 (t, 2H, N—CH$_2$CH$_2$CH$_2$O), 4.6 (m, 4H, N—CH$_2$CH$_2$O), 5.08 (s, 2H, CH$_2$O), 7.25 (d, 1H, 5-H(pyridinone)), 8.2 (d, 1H, 6-H(pyridinone))

Anal. Calcd. for C$_9$H$_{14}$NO$_4$Cl: C, 45.87; H, 5.99; N, 5.94%. Found: C, 45.87; H, 6.02; N, 5.75%.

EXAMPLE 36

1-(3-hydroxypropyl)-2-(1-hydroxyethyl)-3-hydroxy-pyridin-4(1H)-one hydrochloride In an analogous hydrogenation procedure in the preparation of 1-methyl-2-hydroxymethyl-3-hydroxy-pyridin-4(1H)-one hydrochloride, using 8-oxo-4,8-dihydro-2-phenyl-4-methyl-5-(3-hydroxypropyl)-4H-pyridino[3,2-d]-m-dioxin (1.3 g, 4.3 mmol) and 5% Pd/C catalyst (0.3 g) yield the title compound 0.88 g (82%) after recrystallisation from methanol/diethyl ether, as a yellow crystalline solid. m.p. 117–120° C.

$^1$H-NMR (DMSO-d$_6$) δ: 1.5 (d, 3H, CHCH$_3$), 1.65–2.45 (m, 2H, N—CH$_2$CH$_2$CH$_2$O), 3.45 (t, 2H, N—CH$_2$CH$_2$CH$_2$O), 4.65 (m, 4H, N—CH$_2$CH$_2$CH$_2$O), 5.5 (s, 2H, CHCH$_3$), 7.3 (d, 1H, 5-H(pyridinone)), 8.18 (d, 1H, 6-H(pyridinone)), 7.3–9.4 (br., 4H, OH)

Anal. Calcd. for C$_{10}$H$_{16}$NO$_4$Cl: C, 48.10; H, 6.46; N, 5.61%. Found: C, 48.39; H, 6.32; N, 5.62%.

Orally Active Prodrug of the Invention

EXAMPLE 37

1-[(3-Benzoyloxy)propyl]-2-hydroxymethyl-3-hydroxy-pyridin-4(1H)-one hydrochloride (Ester prodrug of the invention)

8-Oxo-4,8-dihydro-2-phenyl-5-[(3-benzoyloxy)propyl]-4H-pyridino[3,2-d]-m-dioxin (4.1 g, 10 mmol) was dissolved in 50 ml of DMF and adjusted to pH 1 with concentrated hydrochloric acid prior to hydrogenolysis for 6 hours in the presence of 5% Pd/C catalyst (1.0 g). Filtration followed by rotary evaporation in vacuo gave the crude product as a white solid. Recrystallization from methanol/diethyl ether gave the pure title compound (2.9 g, 85%) as a white crystalline solid. m.p. 142–143° C.

$^1$H-NMR (DMSO-d$_6$) δ: 1.9–2.8 (m, 2H, N—CH$_2$CH$_2$CH$_2$O), 4.0–5.0 (m, 4H, N—CH$_2$CH$_2$CH$_2$O), 4.8 (s, 2H, CH$_2$O), 7.2–8.1 (m, 6H, Ar & 5-H(pyridinone)), 8.3 (d, 1H, 6-H(pyridinone)), 8.5–10.2 (br., 3H, OH)

Anal. Calcd. for C$_{16}$H$_{18}$NO$_5$Cl: C, 56.56; H, 5.34; N, 4.12%. Found: C, 56.40; H, 5.26; N, 4.08%.

De-Alkylated Active Metabolites of Orally Active Compounds of the Invention

EXAMPLE 38

1-Ethyl-2-hydroxymethyl-3-hydroxy-6-methyl-pyridin-4(1H)-one hydrochloride 1.3 g (4 mmol) 1-ethyl-2-methoxymethyl-3-benzyloxy-6-methyl-pyridin-4(1H)-one hydrochloride was added to 40 ml of 4N hydrochloric acid and refluxed for 6 hours. Concentration to dryness in vacuo afforded the crude product. Recrystallisation from methanol/diethyl ether gave the pure title compound (0.7 g, 80%) as a yellow crystalline solid. m.p. 160–162° C.

$^1$H-NMR (DMSO-d$_6$) δ: 1.3 (t, 3H, N—CH$_2$CH$_3$), 2.5 (s, 3H, 6-CH$_3$), 4.3 (q, 2H, N—CH$_2$CH$_3$), 4.6 (s, 2H, 2-CH$_2$O), 7.1 (s, 1H, 5-H(pyridinone)), 7.8–10.0 (br., 3H, OH)

Anal. Calcd. for C$_9$H$_{14}$NO$_3$Cl.1/4H$_2$O: C, 48.22; H, 6.52; N, 6.25%. Found: C, 48.44; H, 6.37; N, 6.15%.

EXAMPLE 39

1-Ethyl-2-hydroxymethyl-3-hydroxy-pyridin-4(1H)-one hydrochloride 2.0 g (7.33 mmol) 1-ethyl-2-methoxymethyl-3-benzyloxy-pyridin-4(1H)one was dissolved in 50 ml of 4N hydrochloric acid and refluxed for 6 hours. Concentration to dryness in vacuo afforded the crude product. Recrystallisation from methanol/diethyl ether gave the pure title compound (1.1 g, 73%) as a white crystalline solid. m.p. 168–169° C.

$^1$H-NMR (D$_2$O) δ: 1.45 (t, 3H, N—CH$_2$CH$_3$), 4.4 (q, 2H, N—CH$_2$CH$_3$), 4.88 (s, 2H, 2-CH$_2$O), 7.1 (d, 1H, 5-H(pyridinone)), 8.1 (d, 1H, 6-H(pyridinone))

Anal. Calcd. for C$_8$H$_{12}$NO$_3$Cl: C, 46.73; H, 5.88; N, 6.81%. Found: C, 46.71; H, 5.97; N, 7.01%.

Orally Active Prodrugs of the Invention

EXAMPLE 40

1,6-Dimethyl-2-methoxymethyl-3-hydroxy-pyridin-4(1H)-one hydrochloride 1,6-Dimethyl-2-methoxymethyl-3-benzyloxy-pyridin-4(1 H)-one hydrochloride (1.55 g, 5 mmol) was dissolved in methanol (40 ml)/water (10 ml) and hydrogenated for 4 hours in the presence of 5% Pd/C (0.3 g). Following filtration the filtrate was concentrated in vacuo and the crude material recrystallised from methanol/diethyl ether gave the pure title compound (0.95 g, 86.5%) as a white crystalline solid. m.p. 156–159° C.

$^1$H-NMR (DMSO-d$_6$) δ: 2.53 (s, 3H, 6-CH$_3$), 3.28 (s, 3H, OCH$_3$), 3.83 (s, 3H, N—CH$_3$), 4.68 (s, 2H, 2-CH$_2$OCH$_3$), 7.25 (s, 1H, 5-H(pyridinone)), 6.0–8.5 (br., 2H, OH)

Anal. Calcd. for C$_9$H$_{14}$NO$_3$Cl: C, 49.21; H, 6.42; N, 6.38%. Found: C, 49.33; H, 6.49; N, 6.16%.

EXAMPLE 41

1,6-Dimethyl-2-(1-methoxyethyl)-3-hydroxy-pyridin-4(1H)-one hydrochloride

In an analogous hydrogenation procedure in the preparation of 1,6-dimethyl-2-methoxymethyl-3-hydroxy-pyridin-4(1H)-one hydrochloride using 1,6-dimethyl-2-(1-methoxyethyl)-3-benzyloxy-pyridin-4(1H)-one hydrochloride (1.62 g, 5 mmol) and 5% Pd/C catalyst (0.35 g) yield the title compound 1.06 g (90%) after recrystallisation from methanol/diethyl ether, as a white crystalline solid. m.p. 205–207° C.

$^1$H-NMR (DMSO-d$_6$) δ: 1.5 (d, 3H, CHCH$_3$), 2.56 (s, 3H, 6-CH$_3$), 3.24 (s, 3H, OCH$_3$), 4.05 (s, 3H, N—CH$_3$), 5.4 (q, 1H, CHCH$_3$), 7.4 (s, 1H, 5-H(pyridinone)), 8.5–10.0 (br., 2H, OH)

Anal. Calcd. for C$_{10}$H$_{16}$NO$_3$Cl: C, 51.40; H, 6.90; N, 5.99%. Found: C, 51.61; H, 6.76; N, 5.89%.

EXAMPLE 42

1-Ethyl-2-methoxymethyl-3-hydroxy-6-methyl-pyridin-4(1H)-one hydrochloride

In an analogous hydrogenation procedure in the preparation of 1,6-dimethyl-2-methoxymethyl-3-hydroxy-pyridin-4

(1H)-one hydrochloride using 1-ethyl-2-methoxymethyl-3-benzyloxy-6-methyl-pyridin-4(1H)-one hydrochloride (1.3 g, 4 mmol) and 5% Pd/C catalyst (0.3 g) yield the title compound 0.78 g (83%) after recrystallisation from methanol/diethyl ether, as a white crystalline solid. m.p. 174–176° C.

$^1$H-NMR (DMSO-d$_6$) δ: 1.47 (t, 3H, N—CH$_2$CH$_3$), 2.7 (s, 3H, 6-CH$_3$), 3.4 (s, 3H,OCH$_3$), 4.4 (q, 2H, N—CH$_2$CH$_3$), 4.76 (s, 2H, 2-CH$_2$OCH$_3$), 7.35 (s, 1H, 5-H(pyridinone))
Anal. Calcd. for C$_{10}$H$_{16}$NO$_3$Cl: C, 51.40; H, 6.90; N, 5.99%. Found: C, 51.31; H, 7.11; N, 6.04%.

EXAMPLE 43

1,6-Dimethyl-2-(1-methoxypropyl)-3-hydroxy-pyridin-4(1H)-one hydrochloride 1,6-Dimethyl-2-(1-methoxypropyl)-3-benzyloxy-pyridin-4-(1H)-one (1.65 g, 5.5 mmol) was dissolved in methanol (30 ml)/water (10 ml) and adjusted to pH 1 with concentrated hydrochloric acid prior to hydrogenolysis for 4 hours in the presence of 5% Pd/C catalyst (0.35 g). Filtration followed by rotary evaporation gave the crude product as a white solid. Recrystallization from methanol/diethyl ether gave the pure title compound (1.08 g, 79.3%) as a white crystalline solid. m.p. 225–227° C.

$^1$H-NMR (DMSO-d$_6$) δ: 0.9 (t, 3H, CHCH$_2$CH$_3$), 1.4–2.3 (m, 2H, CHCH$_2$CH$_3$), 2.6 (s, 3H, 6-CH$_3$), 3.28 (s, 3H, OCH$_3$), 4.04 (s, 3H, N—CH$_3$), 5.15 (t, 1H, CHCH$_2$CH$_3$), 7.4 (s, 1H, 5-H (pyridinone))
Anal. Calcd. for C$_{11}$H$_{13}$NO$_3$Cl: C, 53.33; H, 7.32; N, 5.65%. Found: C, 53.30; H, 7.18; N, 5.56%.

EXAMPLE 44

1,6-Dimethyl-2-(1-ethoxyethyl)-3-hydroxy-pyridin-4(1H)-one hydrochloride 1,6-Dimethyl-2-(1-ethoxymethyl)-3-benzyloxy-pyridin4(1H)-one (3.65 g, 12 mmol) was dissolved in 40 ml of ethanol and adjusted to pH 1 with concentrated hydrochloric acid prior to hydrogenolysis for 4 hours in the presence of 5% Pd/C catalyst (0.8 g). Filtration followed by rotary evaporation gave the crude product as a white solid. Recrystallization from ethanol/diethyl ether gave the pure title compound (2.48 g, 83.3%) as a white crystalline solid. m.p. 195–199° C.

$^1$H-NMR (CDCl$_3$) δ: 1.2 (t, 3H, OCH$_2$CH$_3$), 1.6 (d, 3H, CHCH$_3$), 2.65 (s, 3H, 6-CH$_3$), 3.5 (q, 2H, OCH$_2$CH$_3$), 4.1 (s, 3H, N—CH$_3$), 5.5 (q, 1H, CHCH$_3$), 5 7.4 (s, 1H, 5-H(pyridinone))
Anal. Calcd. for C$_{11}$H$_{18}$NO$_3$Cl: C, 53.33; H, 7.32; N, 5.65%. Found: C, 53.46; H, 7.16; N, 5.56%.

Novel Intermediates for Synthesis of Amide Compounds of the Invention

EXAMPLE 45

2-Formyl-3-benzyloxy-6-methyl-pyran-4(1H)-one

To a solution of 2-hydroxymethyl-3-benzyloxy-6-methyl-pyran-4(1h)-one (5.28 g, 21.5 mmol, 1 eq) in 100 ml chloroform was added 27 ml of dimethyl sulfoxide and 18.5 ml of triethylamine and the reaction mixture was cooled with an ice-bath to an internal temperature of 3–5° C. Then sulfur trioxide pyridine complex (17.1 g 107 mmol, 5 eq) was added and the mixture was allowed to thaw to room temperature. After stirring for overnight at room temperature, the reaction mixture was washed with water (2×50 ml) and the organic phase was dried over Na$_2$SO$_4$, filtered and concentrated in vacuo to yield an organe oil. Further purification by column chromatography on silica gel (eluant: Et2O) furnished the pure product (4.6 g, 87.7%) as a white crystalline solid. m.p. 78–81 ° C.

$^1$H-NMR (CDCl$_3$) δ: 2.3 (s, 3H, 6-CH$_3$), 5.4 (s, 2H, CH$_2$Ph), 6.2 (s, 1H, 5-H(pyranone)), 7.28 (s, 5H, Ar), 9.75 (s, 1H, CHO)
Anal. Calcd. for C$_{14}$H$_{12}$O$_4$: C, 68.84; H, 4.95%. Found: C, 68.96; H, 5.07%.

EXAMPLE 46

2-Carboxy-3-benzyloxy-6-methyl-pyran-4(1H)-one

2-Formyl-3-benzyloxy-6-methyl-pyran-4(1H)-one (3.67 g, 15.03 mmol, 1 eq) was dissolved in acetone (50 ml) and the solution diluted with water (50 ml). To the reaction mixture was added sulfamic acid (2.04 g, 21.04 mmol, 1.4 eq) and 80% sodium chlorite (1.78 g, 15.8 mmol, 1.05 eq) and allowed to stir for 1 hour at room temperature in an open vessel. Removal of acetone in vacuo yielded crude product as a precipitate in the remaining aqueous solution. The solid was collected, washed with absolute ethanol and dried (3.32 g, 85%). m.p. 173–175° C.

$^1$H-NMR (DMSO-d$_6$) δ: 2.32 (s, 3H, 6-CH$_3$), 5.18 (s, 2H, CH$_2$Ph), 6.2 (s, 1H, 5-H(pyranone)), 7.1–7.6 (m, 5H, Ar)
Anal. Calcd. for C$_{14}$H$_{12}$O$_5$: C, 64.6; H, 4.6%. Found: C, 64.7; H, 4.9%.

EXAMPLE 47

3-(2-Carbonyl-3-benzyloxy-6-methyl-4(1H)-pyran-2-yl)-1,3-thiazolidine-2-thione

2-Carboxy-3-benzyloxy-6-methyl-pyran-4(1H)-one (2.78 g, 10 mmol, 1 eq) was dissolved in 100 ml dichloromethane and the solution stirred vigorously. Dicyclohexylcarbodiimide (DCCI) (2.3 g, 11 mmol, 1.1 eq) was then added followed by the addition of 2-mercaptothiazoline (1.32 g, 11 mmol, 1.1 eq) and a catalytic amount of 4-dimethylaminopyridine (DMAP) (50 mg). The mixture was stirred for 24 h, the white precipitate N,N'-dicyclohexylurea (DCU) filtered from the yellow solution and the filtrate volume was adjusted to 200 ml with CH$_2$Cl$_2$. The dichloromethane layer was washed with 3×100 ml 0.1N sodium hydroxide solution, 100 ml water, dried (Na$_2$SO$_4$), and concentrated in vacuo to yield the crude product as a yellow oil. Further purification by column chromatography on silica gel (eluant: EtOAc) furnished the pure product as a bright yellow oil (2.56 g, 71%).

$^1$H-NMR (CDCl$_3$) δ: 2.28 (s, 3H, 6-CH$_3$), 3.1 (t, 2H, CH$_2$N), 4.35 (t, 2H, CH$_2$S), 5.3 (s, 2H, CH$_2$Ph), 6.25 (s, 1 H, 5-H(pyranone)), 7.28 (s, 5 H, Ar)
Anal. Calcd. for C$_{17}$H$_{15}$NO$_4$S$_2$: C, 56.49; H, 4.18%. Found: C, 56.98; H, 4.52%.

EXAMPLE 48

3-Benzyloxy-6-methyl-4(1H)-pyranone-2-carboxy-(N-methyl)-amide

To a solution of 3-(2-carbonyl-3-benzyloxy-6-methyl-4 (1H)-pyran-2-yl)-1,3-thiazolidine-2-thione (3.61 g, 10 mmol, 1 eq) in 100 ml dichloromethane wad added 10 ml (20 mmol, 2 eq.) of 2M methylamine in THF and the reaction mixture allowed to stir for 2 h. The dichloromethane layer was washed with 3×50 ml 01.N sodium hydroxide solution, 50 ml water, dried ($Na_2SO_4$), and the solvent removed in vacuo. The crude product was further purified by column chromatography on silica gel (eluant: EtOAc) furnished the pure product as a light yellow oil (2.4 g, 88%).

$^1$H-NMR ($CDCl_3$) δ: 2.3 (s, 3H, 6-$CH_3$), 2.7 (d, 3H, $CH_3NH$), 5.28 (s, 2H, $CH_2Ph$), 6.27 (s, 1H, 5-H (pyranone)), 7.3 (s, 5H, Ar)

EXAMPLE 49

3-Benzyloxy-6-methyl-4(1H)-pyranone-2-carboxy-(N-isopropyl)-amide

In an analogous procedure in the preparation of 3-benzyloxy-6-methyl-4(1H)-pyranone-2-carboxy-(N-methyl)-amide using isopropylamine (1.5 eq) yielded the title compound as a yellow oil. Further purification by column chromatography on silica gel (eluant: EtOAc) furnished the pure product as a light yellow oil (yield 88%).

$^1$H-NMR ($CDCl_3$) δ: 1.0 (d, 6H, $CH(CH_3)_2$), 2.4 (s, 3H, 6-$CH_3$), 3.7–4.5 (m, 1H, CHNH), 5.4 (s, 2H, $CH_2Ph$), 6.25 (s, 1H, 5-H(pyranone)), 7.4 (s, 5H, Ar)

EXAMPLE 50

3-Benzyloxy-6-methyl-4(1H)-pyranone-2-carboxy-(N-2'-methoxyethyl)-amide

In an analogous procedure in the preparation of 3-benzyloxy-6-methyl-4(1H)-pyranone-2-carboxy-(N-methyl)-amide using 2-methoxyethylamine (1.5 eq) yielded the title compound after purification by column chromatography on silica gel (eluant: EtOAc) as a light yellow oil (yield 94%).

$^1$H-NMR ($CDCl_3$) δ: 2.25 (s, 3H, 6-$CH_3$), 3.2 (s, 3H, $OCH_3$), 3.0–3.6 (m, 4H, $CH_2CH_2$), 5.28 (s, 2H, $CH_2Ph$), 6.1 (s, 1H, 5-H(pyranone)), 7.26 (s, 5H, Ar), 7.5–8.2 (br., 1H, NH)

EXAMPLE 51

3-Benzyloxy-6-methyl-4(1H)-pyranone-2-carboxy-(N-2'-hydroxyethyl)-amide

In an analogous procedure in the preparation of 3-benzyloxy-6-methyl-4(1H)-pyranone-2-carboxy-(N-methyl)amide using 2-hydroxyethylamine (1.5 eq) yielded the title compound after purification by column chromatography on silica gel (eluant: EtOAc) as a light yellow oil (yield 90%).

$^1$H-NMR ($CDCl_3$) δ: 2.3 (s, 3H, 6-$CH_3$), 3.1–3.8 (m, 4H, $CH_2CH_2$), 5.29 (s, 2H, $CH_2Ph$), 6.15 (s, 1H, 5-H (pyranone)), 7.3 (s, 5H, Ar), 7.5–8.2 (br., 1H, NH)

EXAMPLE 52

3-benzyloxy-6-methyl-4(1H)-pyranone-2-carboxy-(N,N-dimethyl)-amide

In an analogous procedure in the preparation of 3-benzyloxy-6-methyl4(1H)-pyranone-2-carboxy-(N-methyl)-amide using 2M dimethylamine in THF (3 eq) yielded the title compound after purification by column chromatography on silica gel (eluant: EtOAc) as a light yellow oil (yield 88%).

$^1$H-NMR ($CDCl_3$) δ: 2.31 (s, 3H, 6-$CH_3$), 2.88 (s, 3H, $CH_3N$), 3.03 (s, 3H, $CH_3N$), 5.2 (s, 2H, $CH_2Ph$), 6.22 (s, 1H, 5-H(pyranone)), 7.35 (s, 5H, Ar)

Orally Active Prodrugs of the Invention

EXAMPLE 53

1,6-Dimethyl-3-benzyloxy-4(1H)-pyridinone -2-carboxy-(N-methyl)-amide

To a solution of 3-benzyloxy-6-methyl-4(1H)-pyranone-2-carboxy-(N-methyl)-amide (1.37 g, 5 mmol, 1 eq.) in methanol (10 ml) was added 20 ml (40 mmol, 8 eq.) of 2M methylamine in methanol. The reaction mixture was sealed in a thick-walled glass tube and stirred at 70° C. for 12 hours. After removal of the solvent, the residue was purified by column chromatography on silica gel (eluant: 12% $CH_3OH$/88% $CHCl_3$) furnished the pure product (1.1 g, 76.9%) as a white crystalline solid. m.p. 164–165.5° C.

$^1$H-NMR ($CDCl_3$) δ: 2.2 (s, 3H, 6-$CH_3$), 2.65 (d, 3H, $CH_3NH$), 3.47 (s, 3H, N—$CH_3$), 4.92 (s, 2H, $CH_2Ph$), 5.95 (s, 1 H, 5-H(pyridinone)), 7.28 (s, 5H, Ar), 7.9–8.4 (br, 1H, NH)

EXAMPLE 54

1,6-Dimethyl-3-benzyloxy-4(1H)-pyridinone-2-carboxy-(N-isopropyl)-amide

In an analogous procedure in the preparation of 1,6-dimethyl-3-benzyloxy-4(1H)-pyridinone-2-carboxy-(N-methyl)-amide using 1,6-dimethyl-3-benzyloxy-4(1H)-pyridinone-2-carboxy-(N-isopropyl)-amide yielded the crude product. Further purification by column chromatography on silica gel (eluant: 10% $CH_3OH$/90% $CHCl_3$) afforded the pure title compound as a pale yellow crystalline solid (yield, 79%) m.p. 176–178° C.

$^1$H-NMR ($CDCl_3$) δ: 1.2 (d, 6H, $CH(CH_3)_2$), 2.1 (s, 3H, 6-$CH_3$), 3.48 (s, 3H, N-$CH_3$), 3.9–4.5 (m, 1H, CHNH), 4.98 (s, 2H, $CH_2Ph$), 5.98 (s, 1H, 5-H(pyridinone)), 7.22 (s, 5H, Ar), 8.0–8.4 (br, 1H, NH)

EXAMPLE 55

1,6-Dimethyl-3-benzyloxy-4(1H)-pyridinone-2-carboxy-(N-2'-methoxyethyl)-amide

In an analogous procedure in the preparation of 1,6-dimethyl-3-benzyloxy-4(1H)-pyridinone-2-carboxy-(N-methyl)-amide using 1,6-dimethyl-3-benzyloxy-4(1H)-pyridinone-2-carboxy-(N-2'-methoxyethyl)-amide yielded the pure title compound after purification by column chromatography on silica gel (eluant: 10% $CH_3OH$/90% $CHCl_3$) afforded as a white crystalline solid (yield, 82%) m.p. 125–126° C.

$^1$H-NMR ($CDCl_3$) δ: 2.1 (s, 3H, 6-$CH_3$), 3.2 (s, 3H, $OCH_3$), 3.1–3.7 (m, 4H, $CH_2CH_2$), 3.42 (s, 3H, N-$CH_3$), 4.95 (s, 2H, $CH_2Ph$), 6.02 (s, 1H, 5-H(pyridinone)), 7.0–7.5 (m, 5H, Ar), 7.8–8.4 (br, 1H, NH)

EXAMPLE 56

1,6-Dimethyl-3-benzyloxy-4(1H)-pyridinone-2-carboxy-(N-2'-hydroxyethyl)-amide

In an analogous procedure in the preparation of 1,6-dimethyl-3-benzyloxy-4(1H)-pyridinone-2-carboxy-(N-methyl)-amide using 1,6-dimethyl-3-benzyloxy-4(1H)-pyridinone-2-carboxy-(N-2'-hydroxyethyl)-amide yielded the pure title compound after purification by column chromatography on silica gel (eluant: 15% $CH_3OH$/85% $CHCl_3$) afforded as a white crystalline solid (yield, 86%) m.p. 153–155° C.

$^1$H-NMR (CDCl$_3$) δ: 2.1 (s, 3H, 6-CH$_3$), 3.1–3.7 (m, 4H, CH$_2$CH$_2$), 3.42 (s, 3H, N-CH$_3$), 4.95 (s, 2H, CH$_2$Ph), 6.02 (s, 1H, 5-H(pyridinone)), 7.0–7.5 (m, 5H, Ar), 7.8–8.4 (br, 1H, NH)

EXAMPLE 57

1,6-Dimethyl-3-benzyloxy-4(1H)-pyridinone-2-carboxy-(N,N-dimethyl)-amide

In an analogous procedure in the preparation of 1,6-dimethyl-3-benzyloxy-4(1H)-pyridinone-2-carboxy-(N-methyl)amide using 1,6-dimethyl-3-benzyloxy-4(1H)-pyridinone-2-carboxy-(N,N-dimethyl)-amide yielded the pure title compound after purification by column chromatography on silica gel (eluant: 10% CH$_3$OH/90% CHCl$_3$) afforded as a yellow oil (yield, 46%)

$^1$H-NMR (CDCl$_3$) δ: 2.3 (s, 3H, 6-CH$_3$), 2.8 (s, 3H, CH$_3$N), 3.0 (s, 3H, CH$_3$N), 3.42 (s, 3H, N—CH$_3$), 5.2 (q, 2H, CH$_2$Ph, AB center), 6.3 (s, 1H, 5-H(pyridinone)), 7.0–7.5 (m, 5H, Ar)

EXAMPLE 58

1,6-Dimethyl-3-hydroxy-4(1H)-pyridinone-2-carboxy-(N-methyl)-amide hydrochloride 0.86 g of 1,6-dimethyl-3-benzyloxy-4(1H)-pyridinone-2-carboxy-(N-methyl)-amide was dissolved in 30 ml of DMF and hydrogenated at room temperature for 3 hours in the presence of 5% Pd/C catalyst (0.2 g). The catalyst was removed by filtration and the filtrate was acidified to pH 1 with concentrated hydrochloric acid followed by rotary evaporation in vacuo gave the crude product as a white solid. Recrystallization from methanol/diethyl ether gave the pure title compound (0.65 g, 93%) as a white crystalline solid. m.p. 238° C. (dec.)

$^1$H-NMR (DMSO-d$_6$) δ: 2.5 (s, 3H, 6-CH$_3$), 2.7 (d, 3H, CH$_3$NH), 3.7 (s, 3H, N—CH$_3$), 7.2 (s, 1H, 5-H (pyridinone)), 6.8–8.1 (br, 2H, OH), 8.7–9.2 (br, 1H, NH)

Anal. Calcd. for C$_9$H$_{13}$ClN$_2$O$_3$: C, 46.42; H, 5.59; N, 12.03%. Found: C, 46.28; H, 5.71; N, 11.86%.

EXAMPLE 59

1,6-Dimethyl-3-hydroxy-4(1H)-pyridinone-2-carboxy-(N-isopropyl)-amide hydrochloride An analogous hydrogenation procedure to the preparation of 1,6-dimethyl-3-hydroxy-4(1H)-pyridinone-2-carboxy-(N-methyl)-amide hydrochloride, using 1,6-dimethyl-3-benzyloxy-4(1H)-pyridinone-2-carboxy-N-isopropyl)-amide and 5% Pd/C catalyst yielded the title compound (yield, 93%) after recrystallisation from methanol/diethyl ether, as a white crystalline solid. m.p. 219–220° C.

$^1$H-NMR (DMSO-d$_6$) δ: 1.18 (d, 6H, CH(CH$_3$)$_2$), 2.52 (s, 3H, 6-CH$_3$), 3.7 (s, 3H, N—CH$_3$), 3.6–4.4 (m, 1H, CHNH), 5.2–6.5 (br, OH), 7.3 (s, 1H, 5-H(pyridinone)), 8.8–9.2 (br, 1H, NH) Anal. Calcd. for C$_{11}$H$_{17}$ClN$_2$O$_3$: C, 50.63; H, 6.52; N, 10.74%. Found: C, 50.38; H, 6.81;N, 10.56%.

EXAMPLE 60

1,6-Dimethyl-3-hydroxy-4(1H)-pyridinone-2-carboxy-(N-2'-methoxyethyl)-amide

An analogous hydrogenation procedure to the preparation of 1,6-dimethyl-3-hydroxy-4(1H)-pyridinone-2-carboxy-(N-methyl)-amide hydrochloride, using 1,6-dimethyl-3-benzyloxy4(1H)-pyridinone-2-carboxy-(N-2'-methoxyethyl)-amide yielded the title compound (yield, 90%) after recrystallisation from methanol/diethyl ether, as a white crystalline solid. m.p. 204–206° C.

$^1$H-NMR (DMSO-d$_6$) δ: 2.6 (s, 3H, 6-CH$_3$), 3.4 (s, 3H, OCH$_3$), 3.1–3.6 (m, 4H, CH$_2$CH$_2$), 3.8 (s, 3H, N—CH$_3$), 7.35 (s, 1H, 5-H(pyridinone)), 8.8–10.05 (br, OH & NH)

Anal. Calcd. for C$_{11}$H$_{17}$ClN$_2$O$_4$: C, 47.70; H, 6.14; N, 10.12%. Found: C, 47.56; H, 6.30; N, 10.36%.

EXAMPLE 61

1,6-Dimethyl-3-hydroxy-4(1H)-pyridinone-2-carboxy-(N-2'-hydroxyethyl)-amide hydrochloride An analogous hydrogenation procedure to the preparation of 1,6-dimethyl-3-hydroxy-4(1h)-pyridinone-2-carboxy-(N-methyl)-amide hydrochloride, using 1,6-dimethyl-3-benzyloxy-4(1H)-pyridinone-2-carboxy-(N-2'-hydroxyethyl)-amide yielded the title compound (yield, 91%) after recrystallisation from methanol/diethyl ether, as a white crystalline solid. m.p. 178–181° C.

$^1$H-NMR (DMSO-d$_6$) δ: 2.55 (s, 3H, 6-CH$_3$), 3.1–3.7 (m, 4H, CH$_2$CH), 3.85 (s, 3H, N—CH$_3$), 7.25 (s, 1H, 5-H (pyridinone)), 6.7–8.2 (br., OH), 9.1 (t, 1H, NH)

Anal. Calcd. for C$_{10}$H$_{15}$ClN$_2$O$_4$: C, 45.68; H, 5.71; N, 10.66%. Found: C, 45.47; H, 5.98; N, 10.48%.

EXAMPLE 62

1,6-Dimethyl-3-hydroxy-4(1H)-pyridinone-2-carboxy-(N,N-dimethyl)-amide hydrochloride An analogous hydrogenation procedure to the preparation of 1,6-dimethyl-3-hydroxy-4(1H)-pyridinone-2-carboxy-(N-methyl)-amide hydrochloride, using 1,6-dimethyl-3-benzyloxy-4(1H)-pyridinone-2-carboxy-(N,N-dimethyl)-amide yielded the title compound (yield, 94%) after recrystallisation from methanol/diethyl ether, as a white crystalline solid. m.p. 219° C.(dec.)

$^1$H-NMR (DMSO-d$_6$) δ: 2.5 (s, 3H, 6-CH$_3$), 2.8 (s, 3H, CH$_3$N), 3.0 (s, 3H, CH$_3$N), 3.65 (s, 3H, N—CH$_3$), 7.25 (s, 1H, 5-H(pyridinone)), 7.5–9.0 (br., OH)

Anal. Calcd. for C$_{10}$H$_{15}$ClN$_2$O$_3$: C, 48.64; H, 6.08; N, 11.35%. Found: C, 48.58; H, 6.22; N, 11.08%.

EXAMPLE 63

Formulation of Medicaments

| (A) Tablets of the following composition are prepared: | |
|---|---|
| | mg/tablet |
| Compound of formula (I) (micronised) | 250 |
| 'Avicel' (microcrystalline cellulose) | 38 |
| polyvinylpyrrolidone | 3 |
| alginic acid | 6 |
| magnesium stearate | 3 |

The 3-hydroxypyridin-4-one is mixed with 'Avicel' and polyvinylpyrrolidone is added, dissolved in sufficient industrial methylated spirits (74° OP) to produce a mass suitable for granulating. The mass is granulated through a 20 mesh sieve and the resultant granules are dried at a temperature not exceeding 50° C. The dried granules are passed through a 20 mesh sieve and the alginic acid and magnesium stearate are then added and mixed with the granules. The product is compressed into tablets each weighing 300 mg on ⅜ inch flat bevelled edge divided punches.

| (B) Tablets of the following composition are prepared: | |
|---|---|
| | mg/tablet |
| Compound of formula (I) (micronised) | 250 |
| 'Avicel' (microcrystalline cellulose) | 134 |
| polyvinylpyrrolidone | 4 |
| alginic acid | 8 |
| magnesium stearate | 4 |

The tablets are prepared by essentially the same procedure as described in (A) and are compressed at a tablet weight of 400 mg on 7/16 inch flat bevelled edge punches.C)

| Tablets of the following composition are prepared: | |
|---|---|
| | mg/tablet |
| Compound of formula (I) (micronised) | 250 |
| lactose (300 mesh) | 19 |
| maize starch | 15 |
| gelatine | 10 |
| magnesium stearate | 6 |

The 3-hydroxypyridin-4-one is mixed with lactose and half the total quantity of maize starch required, and a 5% solution of gelatine in water is added to the mass. The product is granulated through a 16 mesh sieve, and the resultant granules are dried to constant weight at a temperature not exceeding 50° C. The dried granules are passed through a 20 mesh sieve and mixed with magnesium stearate and the remainder of the maize starch. The product is compressed at a 300 mg tablet weight on ⅜ inch flat bevelled edge divided punches.

EXAMPLE 64

Iron III Mobilisation Efficacy Assay in Rat: Oral Administration

Hepatocytes of manually fasted rats (190–230 g) were labelled with 10 μg $^{59}$Fe ferritin injected iv into the tail vein. One hour later each rat was administered orally with a dose of chelator (150–450 μmol/Kg: see Table 2 below). Control rats were given an equivalent volume of water. The rats were placed in individual metabolic cages and their urine and faeces collected. One hour after the administration they were allowed access to food, with no restriction on water being made throughout the study period. The investigation was terminated 24 hours after the $^{59}$Fe ferritin administration when rats were sacrificed and their livers and gastrointestinal tracts, including all contents including faeces, were removed for gamma counting. Iron mobilisation efficiency is shown in Tables 1 to 3

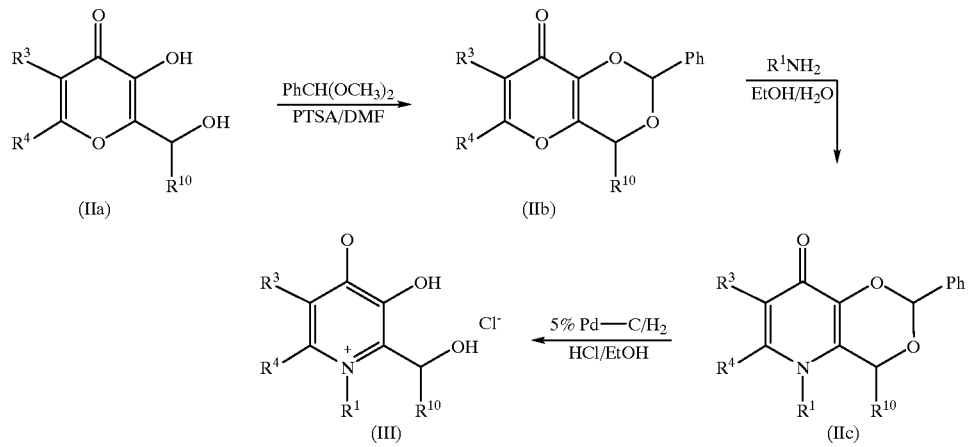

Scheme 1

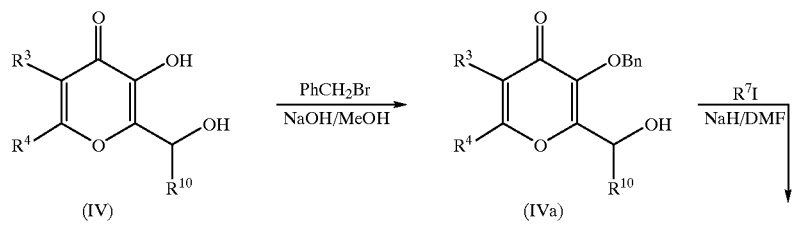

Scheme 2

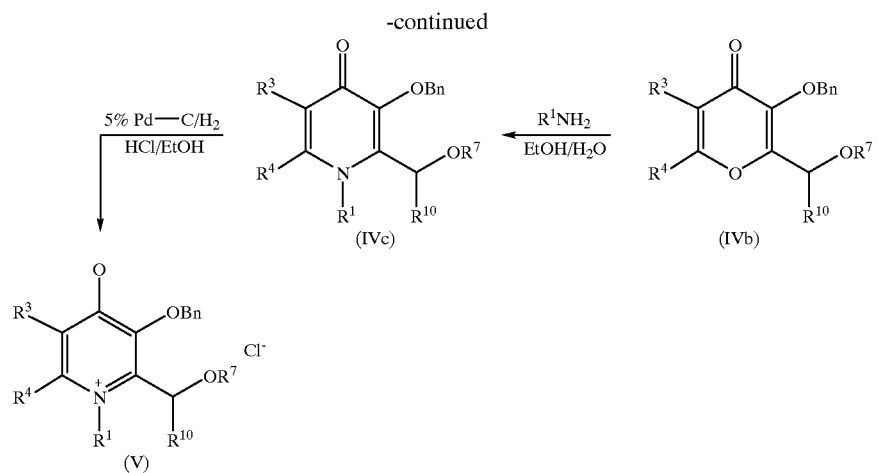
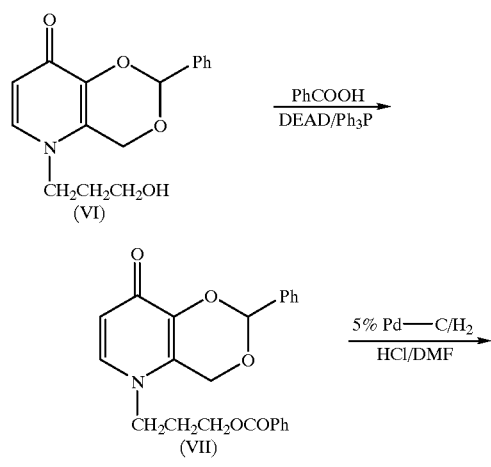
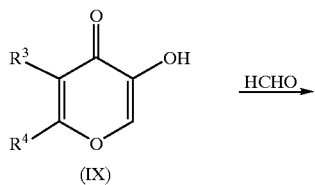
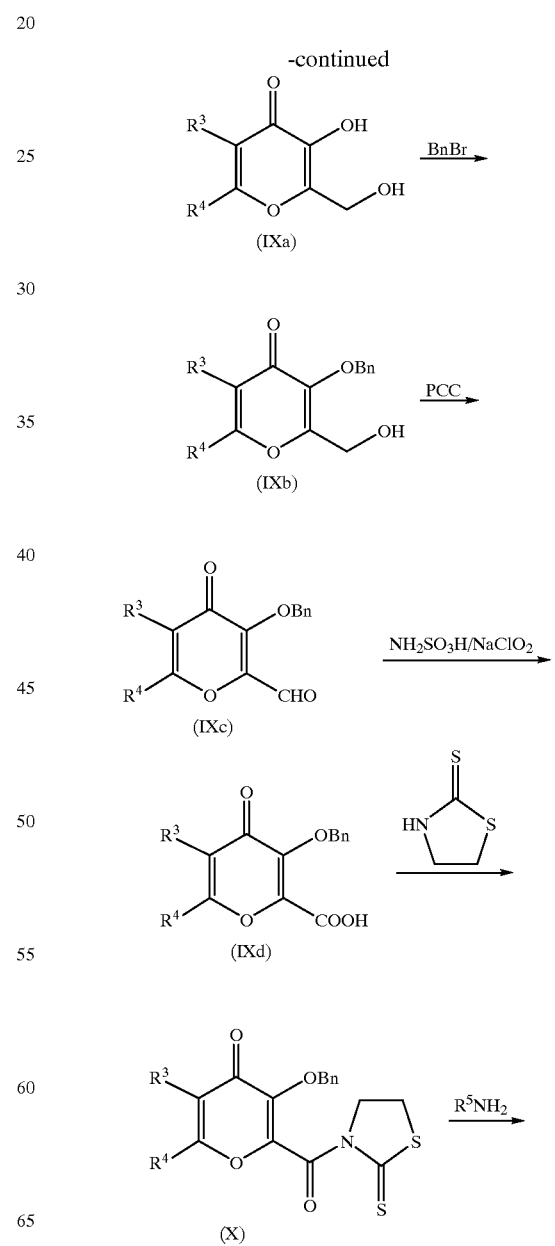

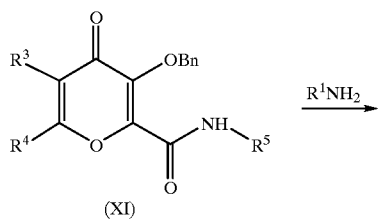
(XI)
$R^1NH_2$ →
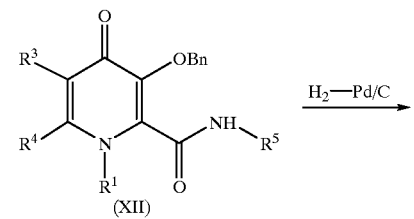
(XII)
$H_2$—Pd/C →
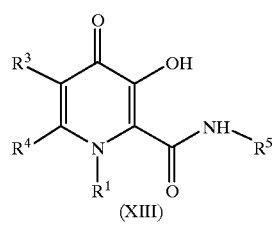
(XIII)
TABLE 1
| Compound | Structure | $D_{pH\ 7.4}$ | pKa | $Log\beta_3$ | pM pH 7.45 | Iron Mobilisation (%) |
|---|---|---|---|---|---|---|
| CP20* | 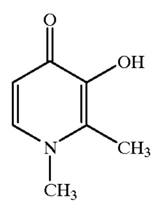 | 0.17 | 3.56, 9.64 (s)<br>3.68, 9.77 (p) | 36.3 | 19.4 | 10.7 ± 3.0%<br>(n = 10) |
| CP94* | 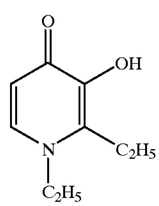 | 1.79 | 3.81, 9.93 (p) | 36.7 | 19.7 | 58.3 ± 9.4%<br>(n = 10) |
| CP41* | 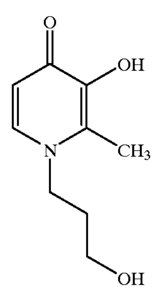 | 0.13 | — | — | — | 29.9 ± 4.3% (n = 5) |

TABLE 1-continued

| Compound | Structure | $D_{pH\ 7.4}$ | pKa | $Log\beta_3$ | pM pH 7.45 | Iron Mobilisation (%) |
|---|---|---|---|---|---|---|
| CP359 | 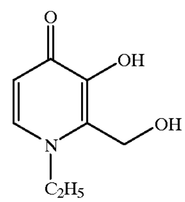 | 0.14 | 2.88, 9.05 (s)<br>2.80, 9.27 (p) | 35.25 | 20.96 | 33.3 ± 6.7% (n = 5) |
| CP360 | 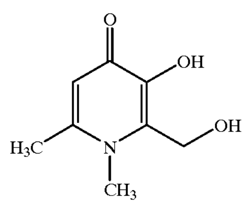 | 0.098 | 3.37, 9.42 (s)<br>3.32, 9.44 (p) | 35.51 | 20.43 | 4.5 ± 1.1% (n = 5) |
| CP361 | 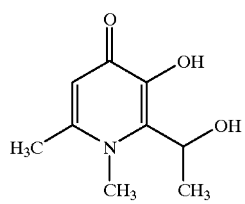 | 0.25 | 3.55, 8.97 (s)<br>3.54, 8.99 (p) | 35.52 | 21.47 | 48.4 ± 7.2%<br>(n = 10) |
| CP362 | 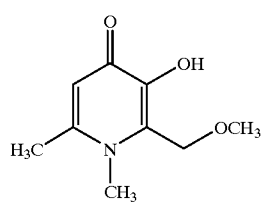 | 0.42 | — | — | — | 51.5 ± 3.7% (n = 5) |
| CP363 | 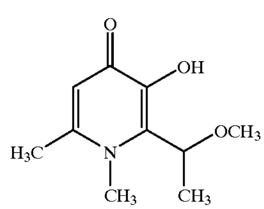 | 1.09 | 3.22, 9.43 (s)<br>3.20, 9.44 (p) | — | — | 73.5 ± 8.1%<br>(n = 10) |
| CP364 | 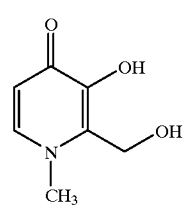 | 0.048 | 2.93, 9.12 (s)<br>3.13, 9.22 (p) | 35.3 | 20.75 | 8.44 ± 3.6% (n = 5) |
| CP365 | 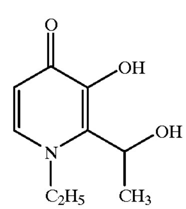 | 0.27 | 3.11, 8.74 (s)<br>3.03, 8.77 (p) | 34.8 | 21.3 | 54.5 ± 9.9% (n = 5) |

TABLE 1-continued

| Compound | Structure | $D_{pH\ 7.4}$ | pKa | Log$\beta_3$ | pM pH 7.45 | Iron Mobilisation (%) |
|---|---|---|---|---|---|---|
| CP366 | 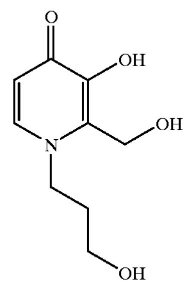 | 0.056 | 2.87, 9.14 (s)<br>3.02, 9.29 (p) | 35.25 | 20.69 | 11.7 ± 4.1% (n = 5) |
| CP367 | 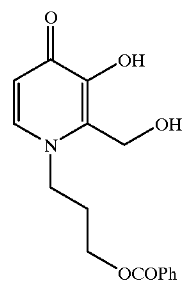 | 5.61 | 2.70, 8.95 (s)<br>2.60, 9.07 (p) | — | — | 56.0 ± 6.0%<br>(n = 10) |
| CP369 | 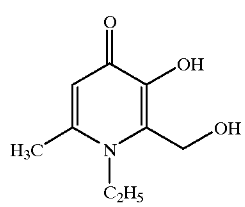 | 0.223 | 3.28, 9.38 (s)<br>3.29, 9.45 (p) | 35.6 | 20.35 | 12.9 ± 2.3% (n = 5) |
| CP370 | 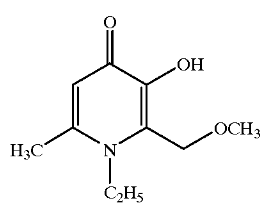 | 1.08 | — | — | — | 41.6 ± 7.5% (n = 5) |
| CP372 | 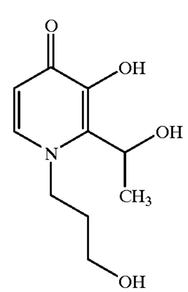 | 0.075 | 2.96, 8.69 (s)<br>2.98, 8.72 (p) | 34.67 | 21.48 | 14.3 ± 4.5% (n = 5) |
| CP373 | 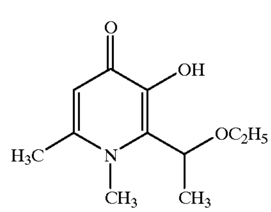 | 3.32 | — | — | — | 39.5 ± 4.8% (n = 5) |

TABLE 1-continued

| Compound | Structure | $D_{pH\ 7.4}$ | pKa | $Log\beta_3$ | pM pH 7.45 | Iron Mobilisation (%) |
|---|---|---|---|---|---|---|
| CP374 | (3-OH, 6-methyl, 1-methyl, 2-(1-hydroxyethyl) pyridin-4-one with C2H5) | 0.73 | 2.78, 8.98 (s) 2.76, 9.00 (p) | 35.03 | 20.95 | 60.4 ± 15.6% (n = 5) |
| CP375 | (3-OH, 6-methyl, 1-methyl, 2-(1-methoxyethyl) pyridin-4-one with C2H5) | 3.85 | — | — | — | 72.0 ± 8.2% (n = 5) |

*= Comparative example of prior art

TABLE 2

Efficacy studies with different doses

| Chelator | Structure | Dose (µmol/kg) | Iron Mobilisation (%) | Efficacy (%) |
|---|---|---|---|---|
| Control | — | — | 3.87 ± 1.0 | — |
| CP20* | (3-OH, 2-CH3, 1-CH3 pyridin-4-one) | 450 | 13.4 ± 5.2 | 9.5 |
|  |  | 300 | 9.2 ± 2.2 | 5.4 |
|  |  | 150 | 6.3 ± 2.1 | 2.4 |
| CP94* | (3-OH, 2-C2H5, 1-C2H5 pyridin-4-one) | 450 | 59.7 ± 10.9 | 55.8 |
|  |  | 300 | 35.7 ± 4.4 | 31.8 |
|  |  | 150 | 16.5 ± 6.2 | 12.6 |
| CP363 | (3-OH, 6-methyl, 1-methyl, 2-(1-methoxyethyl) pyridin-4-one with CH3) | 450 | 73.5 ± 8.1 | 69.6 |
|  |  | 300 | 66.9 ± 8.7 (n = 5) | 63.0 |
|  |  | 150 | 40.7 ± 2.4 (n = 5) | 36.8 |
| CP374 | (3-OH, 6-methyl, 1-methyl, 2-(1-hydroxyethyl) pyridin-4-one with C2H5) | 450 | 60.4 ± 15.6 | 56.5 |
|  |  | 150 | 34.0 ± 4.3 (n = 5) | 30.1 |

TABLE 2-continued

Efficacy studies with different doses

| Chelator | Structure | Dose (μmol/kg) | Iron Mobilisation (%) | Efficacy (%) |
|---|---|---|---|---|
| CP375 | 3-hydroxy-1,6-dimethyl-2-(1-methoxypropyl)-4(1H)-pyridinone | 450<br>150 | 72.0 ± 8.2<br>40.2 ± 8.5 (n = 5) | 68.1<br>36.3 |

*= Comparative Examples of prior art compounds

TABLE 3

| Compd | Structure | $D_{pH\,7.4}$ | PKa | $Log\beta_3$ | pM pH 7.45 | Iron Mobilisation (%) |
|---|---|---|---|---|---|---|
| CP502 | 3-hydroxy-1,6-dimethyl-2-(N-methylcarbamoyl)-4(1H)-pyridinone | 0.04 | 2.64, 8.36 (s)<br>2.83, 8.38 (p) | 35.78 | 23.42 | 62.4 ± 5.0% (n = 5) |
| CP504 | 3-hydroxy-1,6-dimethyl-2-(N-isopropylcarbamoyl)-4(1H)-pyridinone | 0.30 | 2.64, 8.56 (s)<br>2.81, 8.74 (p) | 35.34 | 22.46 | 45.8 ± 6.1% (n = 5) |
| CP506 | 3-hydroxy-1,6-dimethyl-2-(N-(2-methoxyethyl)carbamoyl)-4(1H)-pyridinone | 0.04 | 2.50, 8.35 (s)<br>2.62, 8.34 (p) | 34.88 | 22.57 | 40.9 ± 7.1% (n = 5) |
| CP507 | 3-hydroxy-1,6-dimethyl-2-(N-(2-hydroxyethyl)carbamoyl)-4(1H)-pyridinone | 0.02 | 2.57, 8.19 (s)<br>2.65, 8.28 (p) | 34.63 | 22.73 | 29.2 ± 6.3% (n = 5) |
| CP508 | 3-hydroxy-1,6-dimethyl-2-(N,N-dimethylcarbamoyl)-4(1H)-pyridinone | 0.16 | 2.61, 8.10 (s)<br>2.61, 8.10 (p) | 35.13 | 23.46 | 35.0 ± 9.8% (n = 5) |

TABLE 3-continued

| Compd | Structure | $D_{pH\ 7.4}$ | PKa | $Log\beta_3$ | pM pH 7.45 | Iron Mobilisation (%) |
|---|---|---|---|---|---|---|
| Novartis bidentate ligand (3)* | 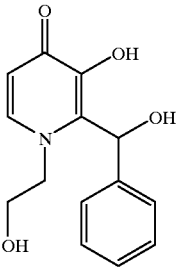 | 2.81 | 2.60, 8.39 (s) 2.59, 8.38 (p) | 35.57 | 23.15 | 50.8 ± 10.3% (n = 5) |

What is claimed is:

1. A 3-hydroxypyridin-4-one compound of formula I

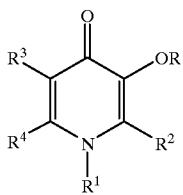

(I)

wherein
R is selected from the group consisting of hydrogen, $C_{1-6}$ alkyl, $C_{7-10}$ aralkyl, —C(O)—$R^8$, and the equivalent sulpho acid ester, wherein $R^8$ is selected from the group consisting of $C_{1-6}$ alkyl and $C_{7-10}$ aralkyl,
$R^1$ is selected from the group consisting of an aliphatic hydrocarbon group and an aliphatic hydrocarbon group substituted by a hydroxy group or a carboxylic acid ester, sulpho acid ester, $C_{1-6}$ alkoxy, $C_6$-aryloxy or $C_{7-10}$ aralkoxy ether thereof,
$R^3$ is selected from the group consisting of hydrogen and $C_{1-6}$ alkyl; wherein
$R^2$ is selected from the group consisting of —CONH—$R^5$ (i)

—CONHCOR$^5$ (ii)

and

—CON(CH$_3$)$_2$, (iii)

$R^4$ is selected from the group consisting of hydrogen, $C_{1-6}$ alkyl, —CR$^6$R$^6$OR$^7$ and a group as described for $R^2$,
$R^5$ is selected from the group consisting of hydrogen and optionally hydroxy, alkoxy, aryloxy or aralkoxy substituted $C_{1-13}$ alkyl, aryl and $C_{7-13}$ aralkyl,
$R^6$ is independently selected from the group consisting of hydrogen and $C_{1-13}$ alkyl,
and $R^7$ is selected from the group consisting of hydrogen, $C_{1-13}$ alkyl, aryl and $C_{7-13}$ aralkyl,
or a pharmaceutically acceptable salt of any such compound.

2. A compound as claimed in claim 1 wherein $R^5$ and $R^7$ are independently selected from $C_{1-6}$ alkyl, aryl and $C_{7-10}$ aralkyl.

3. A compound as claimed in claims 1 wherein $R^6$ is independently selected from hydrogen and $C_{1-6}$ alkyl.

4. A compound as claimed in claim 1 wherein $R^1$ is an aliphatic hydrocarbon group substituted by a hydroxy group or an esterified hydroxy group, the ester acyl group thereof being of formula —CO—$R^9$ where $R^9$ is $C_{1-6}$ alkyl or phenyl.

5. A compound as claimed in claim 1 wherein $R^2$ is a group —CONH—$R^5$.

6. A process for the preparation of a compound of formula (I)

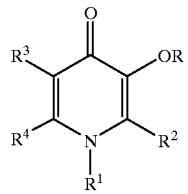

wherein
R is selected from the group consisting of hydrogen or a group that is removed by metabolism in vivo to provide the free hydroxy compound,
$R^1$ is selected from the group consisting of an aliphatic hydrocarbon group and an aliphatic hydrocarbon group substituted by a hydroxy group or a carboxylic acid ester, sulpho acid ester, $C_{1-6}$ alkoxy, $C_6$-aryloxy or $C_{7-10}$aralkoxy ether thereof,
$R^3$ is selected from the group consisting of hydrogen and $C_{1-6}$ alkyl; wherein
$R^2$ is selected from the group consisting of —CONH—$R^5$ (i)

—CONHCOR$^5$ (ii)

and

—CON(CH$_3$)$_2$, (iii)

$R^4$ is selected from the group consisting of hydrogen, $C_{1-6}$ alkyl, —CR$^6$R$^6$OR$^7$ and a group as described for $R^2$,
$R^5$ is selected from the group consisting of hydrogen and optionally hydroxy, alkoxy, aryloxy or aralkoxy substituted $C_{1-13}$ alkyl, aryl and $C_{7-13}$ aralkyl,
$R^6$ is independently selected from the group consisting of hydrogen and $C_{1-13}$ alkyl,
and $R^7$ is selected from the group consisting of hydrogen, $C_{1-13}$ alkyl, aryl and $C_{7-13}$ aralkyl, or a pharmaceutically acceptable salt of any such compound wherein the process reacts a 2-carboxy compound of formula (IXd),

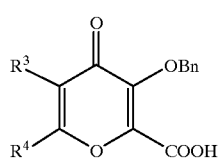

(IXd)

with mercaptothiazoline to provide the corresponding 2-carbonyl-thiazolidine-2-thione of formula (X),

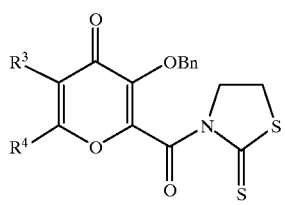

(X)

reacts that with a compound selected from the group consisting of $R^5NH_2$ and $(CH_3)_2NH$ to give a compound selected from the group consisting of the corresponding 2-amido compound of formula (XI) and the corresponding 2-carboxy-(N,N-dimethyl) substituted compound

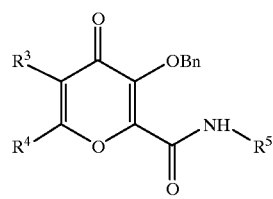

(XI)

and reacts that with a compound $R^1NH_2$ to give a compound selected from the group consisting of the corresponding 2-amido-pyridin-4(1H)-one compound of formula (XII) and the corresponding 2-carboxy-(N,N-dimethyl) substituted compound

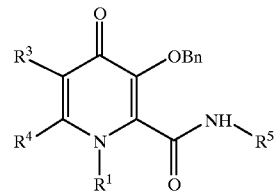

(XII)

7. A process as claimed in claim 6 comprising reducing the compound of formula (XII) to provide the corresponding 2-hydroxyalkyl-pyridin-4(1H)-one.

8. A method of treating a patient in need of therapy for disease selected from those associated with excess iron and presence of iron dependent parasites comprising administering to the patient an amount of a compound as claimed in claim 1, or a pharmaceutically acceptable salt of any such compound, that is effective to remove iron from the patient.

9. A pharmaceutical composition comprising a compound as claimed claim 1 together with a pharmaceutically acceptable carrier.

10. A composition as claimed in claim 9 wherein it is in a form suitable for oral administration.

11. A composition as claimed in claim 10 wherein it is in the form of a tablet, lozenge or capsule.

* * * * *